(12) United States Patent
Winkler et al.

(10) Patent No.: US 10,898,204 B2
(45) Date of Patent: Jan. 26, 2021

(54) OCCLUSION CLIP

(71) Applicant: AtriCure, Inc., Mason, OH (US)

(72) Inventors: Matthew J. Winkler, Liberty Township, OH (US); Kenneth Lance Miller, Hamilton, OH (US)

(73) Assignee: AtriCure, Inc., Mason, OH (US)

( * ) Notice: Subject to any disclaimer, the term of this patent is extended or adjusted under 35 U.S.C. 154(b) by 120 days.

(21) Appl. No.: 15/904,541

(22) Filed: Feb. 26, 2018

(65) Prior Publication Data

US 2018/0317922 A1 Nov. 8, 2018

Related U.S. Application Data

(63) Continuation of application No. 14/085,836, filed on Nov. 21, 2013, now Pat. No. 9,901,351.

(60) Provisional application No. 61/729,023, filed on Nov. 21, 2012.

(51) Int. Cl.
*A61B 17/122* (2006.01)

(52) U.S. Cl.
CPC ........ *A61B 17/122* (2013.01); *A61B 17/1227* (2013.01)

(58) Field of Classification Search
CPC ... A61B 17/12; A61B 17/122; A61B 17/1227; A61F 6/206
See application file for complete search history.

(56) References Cited

U.S. PATENT DOCUMENTS

2011/0046437 A1\* 2/2011 Kassab ................ A61F 5/0086
600/37

\* cited by examiner

*Primary Examiner* — Melanie R Tyson
(74) *Attorney, Agent, or Firm* — Dorton & Willis LLP; Ryan Willis

(57) ABSTRACT

An occlusion clamp including: (a) an occlusion tongs including a primary spring coupling a first longitudinal arm to a second longitudinal arm, the first longitudinal arm including a first linear occlusion surface configured to be parallel to and overlap a second linear occlusion surface of the second longitudinal arm, each of the first and second longitudinal arms having a free distal end; and, (b) a secondary spring removably coupled to the occlusion tongs.

18 Claims, 23 Drawing Sheets

OCCLUSION CLIP

CROSS REFERENCE TO RELATED APPLICATIONS

The present application is a continuation of U.S. patent application Ser. No. 14/085,836, filed Nov. 21, 2013 and titled, "OCCLUSION CLIP," now U.S. Pat. No. 9,901,351, which claims the benefit of U.S. Provisional Patent Application Ser. No. 61/729,023, filed Nov. 21, 2012 and titled, "OCCLUSION CLIP," the disclosure of each of which is hereby incorporated by reference.

RELATED ART

Field of the Invention

The present disclosure is directed to devices used to occlude anatomical structures and, more specifically, to clips that may be used to occlude anatomical structures.

Brief Discussion of Related Art

Embolic stroke is the nation's third leading killer for adults, and is a major cause of disability. There are over 700,000 strokes per year in the United States alone. Of these, roughly 100,000 are hemorrhagic, and 600,000 are ischemic (either due to vessel narrowing or to embolism). The most common cause of embolic stroke emanating from the heart is thrombus formation due to atrial fibrillation. Approximately 80,000 strokes per year are attributable to atrial fibrillation. Atrial fibrillation is an arrhythmia of the heart that results in a rapid and chaotic heartbeat that produces lower cardiac output and irregular and turbulent blood flow in the vascular system. There are over five million people worldwide with atrial fibrillation, with about four hundred thousand new cases reported each year. A patient with atrial fibrillation typically has a decreased quality of life due, in part, to the fear of a stroke, and the pharmaceutical regimen commonly used to reduce that risk.

For patients who develop atrial thrombus from atrial fibrillation, the clot normally occurs in the left atrial appendage (LAA) of the heart. The LAA is a cavity that looks like a small pocket or windsock that is connected to the lateral wall of the left atrium between the mitral valve and the root of the left pulmonary vein. The LAA normally contracts with the rest of the left atrium during a normal heart cycle, thus keeping blood from becoming stagnant therein, but often fails to contract with any vigor in patients experiencing atrial fibrillation due to the discoordinate electrical signals associated with atrial fibrillation. As a result, thrombus formation is predisposed to form in the stagnant blood within the LAA.

Blackshear and Odell reported that of 1288 patients with non-rheumatic atrial fibrillation involved in their study, 221 (17%) had thrombus detected in the left atrium. Blackshear J L, Odell J A., *Appendage Obliteration to Reduce Stroke in Cardiac Surgical Patients With Atrial Fibrillation*. Ann Thorac. Surg., 1996.61(2):755-9. Of the patients with atrial thrombus, 201 (91%) had the atrial thrombus located within the left atrial appendage. The foregoing suggests that the elimination or containment of thrombus formed within the LAA of patients with atrial fibrillation would significantly reduce the incidence of stroke.

Pharmacological therapies for stroke prevention, such as oral or systemic administration of warfarin, may be inadequate due to serious side effects of the medications and lack of patient compliance in taking the medication.

One approach to LAA exclusion is occlusion of the LAA using a permanent clip. Prior art clips have not been permanently attached to the base of the LAA and operate to close off the interior pocket from the atrium. Over time, scar tissue seals the LAA at the point where the tissue is sandwiched between the clip, while scar tissue attempts to grow around the clip to maintain it in position. Prior art clips have been closed ended so that application of the clip to the LAA is more complicated because it requires feeding the LAA in between opposed spring arms, while concurrently feeding the LAA in between biased straight bars.

Despite the various efforts in the prior art, there remains a need for a minimally invasive methods and associated devices for occlusion of the LAA that allow the clip to be placed from the side of the LAA without having to feed the LAA in between a completely bounded perimeter.

Introduction to the Invention

It is a first aspect of the present invention to provide an occlusion clamp comprising: (a) an occlusion tongs including a primary spring coupling a first longitudinal arm to a second longitudinal arm, the first longitudinal arm including a first linear occlusion surface configured to be parallel to and overlap a second linear occlusion surface of the second longitudinal arm, each of the first and second longitudinal arms having a free distal end, and (b) a secondary spring removably coupled to the occlusion tongs.

In a more detailed embodiment of the first aspect, the first longitudinal arm, the spring, and the second longitudinal arm are integrated. In yet another more detailed embodiment, the first longitudinal arm includes a first trench extending longitudinally along a majority of a length of the first longitudinal arm, the second longitudinal arm includes a second trench extending longitudinally along a majority of a length of the second longitudinal arm, at least a first portion of the secondary spring is configured engage the first trench to removably couple the secondary spring to the occlusion tongs, and at least a second portion of the secondary spring is configured to engage the second trench to removably couple the secondary spring to the occlusion tongs. In a further detailed embodiment, the first trench includes a first plurality of cavities and each configured to potentially receive the first portion of the secondary spring to maintain a relative position of the secondary spring with respect to the first longitudinal arm. In still a further detailed embodiment, the second trench includes a second plurality of cavities and each configured to potentially receive the second portion of the secondary spring to maintain a relative position of the secondary spring with respect to the second longitudinal arm. In a more detailed embodiment, the first plurality of cavities is spaced apart from one another. In a more detailed embodiment, the first plurality of cavities is spaced apart from one another and the second plurality of cavities is spaced apart from one another. In another more detailed embodiment, the first longitudinal arm includes a first projection extending longitudinally along a majority of a length of the first longitudinal arm, the second longitudinal arm includes a second projection extending longitudinally along a majority of a length of the second longitudinal arm, at least a first portion of the secondary spring is configured to engage the first projection to removably couple the secondary spring to the occlusion tongs, and at least a second portion of the secondary spring is configured to engage the second projection to removably couple the secondary spring to the occlusion tongs. In yet another more detailed embodiment, the first projection comprises a first plurality of projections and each configured to potentially engage the first portion of the secondary spring to maintain a relative position of the secondary spring with respect to the first longitudinal arm. In still another more detailed embodiment, the second projection comprises a second plurality of projections and each configured to potentially engage the second portion of the secondary spring to maintain a relative position of the secondary spring with respect to the second longitudinal arm.

In yet another more detailed embodiment of the first aspect, the first plurality of projections is spaced apart from one another. In yet another more detailed embodiment, the first plurality of projections is spaced apart from one another and the second plurality of projections is spaced apart from one another. In a further detailed embodiment, the first longitudinal arm includes at least one of a first cavity and a first projection extending longitudinally along a majority of a length of the first longitudinal arm, the second longitudinal arm includes at least one of a second cavity and a second projection extending longitudinally along a majority of a length of the second longitudinal arm, at least a first portion of the secondary spring is configured to engage at least one of the first cavity and the first projection to removably couple the secondary spring to the occlusion tongs, and at least a second portion of the secondary spring is configured to engage at least one of the second cavity and the second projection to removably couple the secondary spring to the occlusion tongs. In still a further detailed embodiment, the first projection comprises a first plurality of projections and each configured to potentially engage the first portion of the secondary spring to maintain a relative position of the secondary spring with respect to the first longitudinal arm, and the second projection comprises a second plurality of projections and each configured to potentially engage the second portion of the secondary spring to maintain a relative position of the secondary spring with respect to the second longitudinal arm. In a more detailed embodiment, the first plurality of projections is spaced apart from one another, and the second plurality of projections is spaced apart from one another. In a more detailed embodiment, the first cavity comprises a first plurality of cavities and each configured to potentially engage the first portion of the secondary spring to maintain a relative position of the secondary spring with respect to the first longitudinal arm, and the second cavity comprises a second plurality of cavities and each configured to potentially engage the second portion of the secondary spring to maintain a relative position of the secondary spring with respect to the second longitudinal arm. In another more detailed embodiment, the first plurality of cavities is spaced apart from one another, and the second plurality of cavities is spaced apart from one another. In yet another more detailed embodiment, the spring comprises a discontinuous ring having a first end and a second end, the first end is spaced apart from the second end, the first end is mounted to the first longitudinal arm, and the second end is mounted to the second longitudinal arm. In still another more detailed embodiment, the first end includes a first planar surface, the second end includes a second planar surface, and the first planar surface extends parallel to the second planar surface.

In a more detailed embodiment of the first aspect, the first longitudinal arm includes a first arcuate boundary defining a first arcuate depression, the second longitudinal arm includes a second arcuate boundary defining a second arcuate depression, and the primary spring interposes the first arcuate boundary and the second arcuate boundary. In yet another more detailed embodiment, the first longitudinal arm, the primary spring, and the second longitudinal arm are fabricated from at least one of a polymer, a composite, concrete, a metal, wood, and a ceramic, the secondary spring is fabricated from at least one of a polymer, a composite, concrete, a metal, wood, and a ceramic. In a further detailed embodiment, the first longitudinal arm, the primary spring, and the second longitudinal arm are fabricated from a polymer, and the secondary spring is fabricated from a metal. In still a further detailed embodiment, the first longitudinal arm, the primary spring, and the second longitudinal arm are fabricated from the same polymer. In a more detailed embodiment, the secondary spring includes a U-shape. In a more detailed embodiment, the secondary spring includes a longitudinal cross section comprising at least one of circular, rectangular, triangular, and oblong. In another more detailed embodiment, the secondary spring comprises a discontinuous loop having a first closed end and a second open end, the second open end being partially defined by a pair of spaced apart legs each having an arcuate projection.

It is a second aspect of the present invention to provide an occlusion clamp comprising: (a) a first jaw including a first occlusion surface; (b) a second jaw repositionably mounted to the first jaw, the second jaw including a second occlusion surface; (c) a primary spring removably coupled to the first jaw and the second jaw to exert a first bias acting on proximal ends of the first and second jaws; and, (d) a secondary spring removably coupled to the first jaw and the second jaw to exert a second bias acting on distal ends of the first and second jaws.

In a more detailed embodiment of the second aspect, the second jaw is configured to be pivotally and radially repositionably mounted to the first jaw. In yet another more detailed embodiment, the occlusion clamp further includes a pin mounted to the second jaw, wherein the first jaw includes an orifice sized to allow at least partial throughput of the pin and radial movement of the pin within a boundary of the orifice. In a further detailed embodiment, at least a portion of the pin includes a circular cross-section, and the second jaw includes a cavity configured to receive a projection of the pin in a friction fit to mount the pint to the second jaw. In still a further detailed embodiment, at least a portion of the pin includes a circular cross-section, and the second jaw includes a projection configured to be received by a cavity of the pin to mount the pin to the second jaw via a friction fit. In a more detailed embodiment, the first jaw includes a first elongated platform having a dominant lengthwise dimension, and the second jaw includes a second elongated platform having a dominant lengthwise dimension and configured to vertically overlap the first elongated platform. In a more detailed embodiment, the first jaw includes a first hub extending from the first elongated platform in the lengthwise dimension, the first hub having a widthwise dimension perpendicular to the lengthwise dimension that is less than a widthwise dimension of the first elongated platform, the first hub includes a height dimension perpendicular to the lengthwise dimension and the widthwise dimension, the height dimension of the first hub being greater than a height dimension of the first elongated platform, the second jaw includes a second hub extending from the second elongated platform in the lengthwise dimension, the second hub having a widthwise dimension perpendicular to the lengthwise dimension that is less than a widthwise dimension of the second elongated platform, and the second hub includes a height dimension perpendicular to the lengthwise dimension and the widthwise dimension, the height dimension of the second hub being greater than a height dimension of the second elongated platform. In another more detailed embodiment, the first jaw includes a first hub extending from the first elongated platform, the second jaw includes a second hub extending from the second elongated platform, and the first hub is configured to horizontally overlap the second hub. In yet another more detailed embodiment, the first jaw includes a first elongated platform and a first hub, the second jaw includes a second elongated platform and a second hub, the first hub includes a cavity sized to house the primary spring, and the primary spring is concurrently mounted to the first hub and at least one of the second hub and the pin. In still another more detailed embodiment, the primary spring includes a U-shaped portion.

In yet another more detailed embodiment of the second aspect, the primary spring comprises a discontinuous loop. In yet another more detailed embodiment, the primary spring comprises a continuous loop. In a further detailed embodiment, the primary spring is fabricated from at least one of a polymer, a composite, and a metal. In still a further detailed embodiment, the primary spring is configured to exert a first bias to retard radial repositioning between the first jaw and the second jaw, and the secondary spring is configured to exert a second bias to retard pivotal repositioning between the first jaw and the second jaw. In a more detailed embodiment, the secondary spring includes a U-shaped portion. In a more detailed embodiment, the secondary spring comprises a discontinuous loop. In another more detailed embodiment, the first jaw includes a first trench, the second jaw includes a second trench, and the secondary spring is configured to be received concurrently with the first trench and the second trench when coupled to the first jaw and the second jaw. In yet another more detailed embodiment, the first jaw includes a first projection, the second jaw includes a second projection, and the secondary spring is configured to concurrently receive the first projection and the second projection when coupled to the first jaw and the second jaw. In still another more detailed embodiment, the first jaw includes a substantially planar first occlusion surface, the second jaw includes a substantially planar second occlusion surface, a lengthwise dimension of the first occlusion surface is larger than a widthwise dimension perpendicular to the lengthwise dimension, a lengthwise dimension of the second occlusion surface is larger than a widthwise dimension perpendicular to the lengthwise dimension. In a more detailed embodiment of the third aspect, the secondary spring is fabricated from at least one of a polymer, a composite, and a metal.

DETAILED DESCRIPTION

Figure 1:
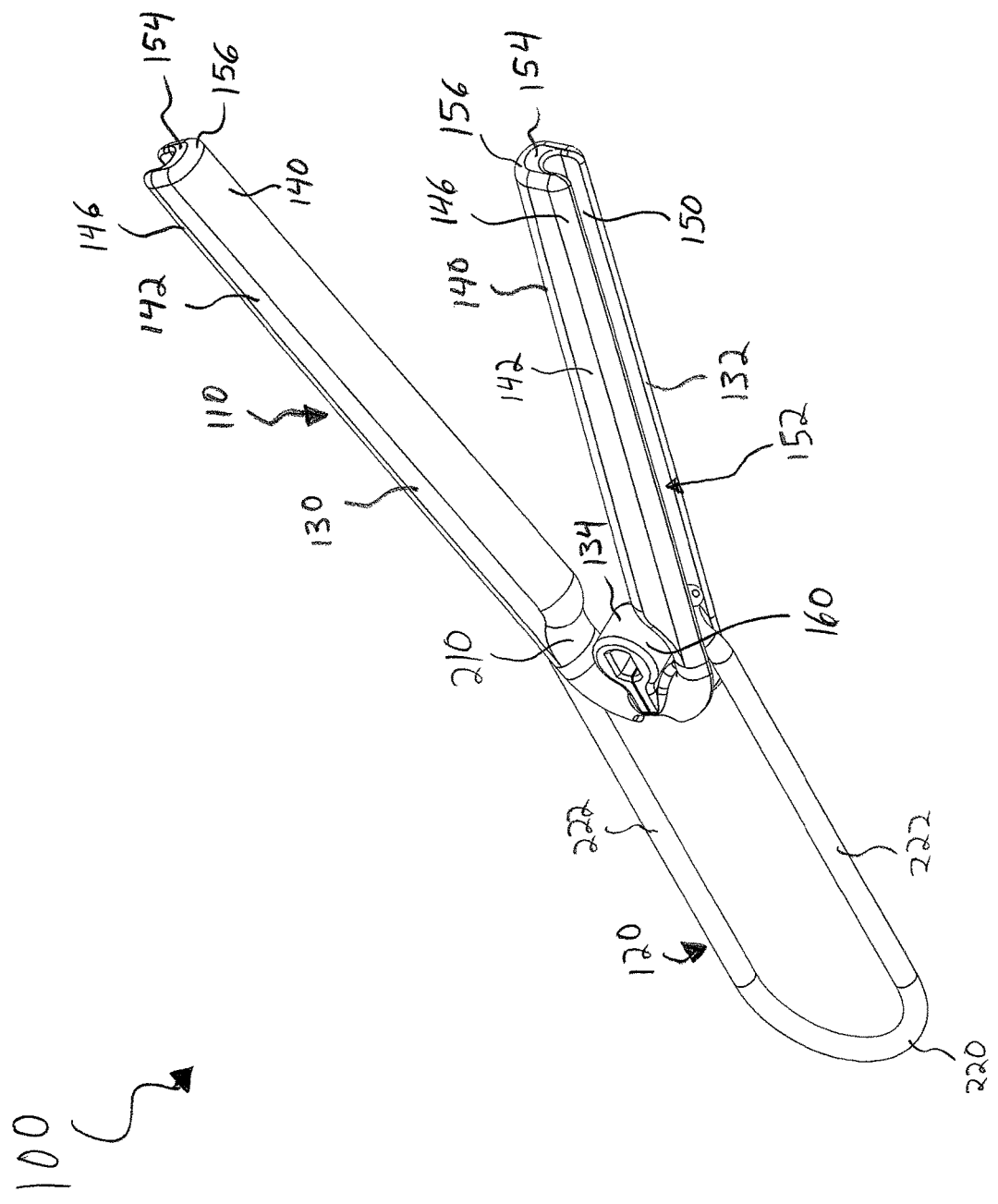
FIG. 1 is an elevated perspective view of a first exemplary occlusion clip in accordance with the instant disclosure.

The exemplary embodiments of the present disclosure are described and illustrated below to encompass devices, methods, and techniques for fabricating, operation of, and implanting an occlusion clip. Of course, it will be apparent to those of ordinary skill in the art that the embodiments discussed below are exemplary in nature and may be reconfigured without departing from the scope and spirit of the present disclosure. However, for clarity and precision, the exemplary embodiments as discussed below may include optional steps, methods, and features that one of ordinary skill should recognize as not being a requisite to fall within the scope of the present disclosure. Accordingly, it should be understood that the following detailed description of embodiments of the present disclosure are exemplary in nature and are not intended to constitute limitations upon the present invention. It is also to be understood that variations of the exemplary embodiments contemplated by one of ordinary skill in the art shall concurrently fall within the scope and spirit of the invention.

Referencing FIGS. 1-8, a first exemplary occlusion clip 100 includes tongs 110 that are repositionable with respect to a secondary spring 120. In this exemplary embodiment, the tongs 110 may be fabricated from various materials such as, without limitation, a biologic material, a biologically reabsorbable material, a plastic, a metal, a metal alloy, and carbon fiber. In further exemplary form, the material may be formulated, include additives, or naturally be reabsorbable by a mammalian body within a predetermined period of time, such as six months or longer.

The secondary spring 120 may be fabricated from various such as, without limitation, a biologic material, a biologically reabsorbable material, a plastic, a metal, a metal alloy, and carbon fiber.

In exemplary form, the tongs 110 include a first longitudinal segment 130 that is mounted to a second longitudinal segment 132 by way of a primary spring 134. The primary spring 134 operates to bias a proximal portion of both the first and second longitudinal segments 130, 132 toward one another, while a distal portion of both the first and second longitudinal segments are biased toward one another using the secondary spring 120. In this exemplary embodiment, each longitudinal segment 130, 132 is a mirror image of the other and comprises a generally linear arm extending from the primary spring 134. But it should also be noted that the longitudinal segments need not be mirror images of one another.

A first exterior surface 140 of the longitudinal segments 130, 132 is substantially convex and includes a semicircular cross-section perpendicular to the longitudinal length thereof. This first surface seamlessly transitions into a pair of lateral surfaces 142, 144 that extend substantially parallel to one another and spaced apart from one another the width of the segment. Each lateral surface 142, 144 terminates at a respective rounded edge 146, 148 that transitions into a concave interior surface 150. The concave interior surface 150 has a substantially uniform, semicircular cross-section perpendicular to the longitudinal length thereof and provides a linear, longitudinal channel 152 within which a portion of the secondary spring 120 traverses. The three exterior surfaces 140, 142, 144 and the interior surface 150 longitudinally converge at a distal end 154 that is substantially planar and perpendicular with respect to the exterior surfaces and interior surface, but for a rounded transition 156 linking the surfaces to one another.

Opposite the distal ends 154 of the longitudinal segments 130, 132 is the primary loop spring 134. In this exemplary embodiment, the primary spring 134 is integrally formed with the longitudinal segments 130, 132 and, in this fashion, provides a seamless transition therebetween. The primary spring 134 includes a central discontinuous loop 160 having an outer circumferential surface 162 with a substantially constant outer diameter until reaching a bottleneck 164. This bottleneck 164 connects the discontinuous loop 160 to proximal arcuate housing segments 166, 168, that themselves are coupled to the longitudinal segments 130, 132.

Referring back to the discontinuous loop 160, lateral and medial ends of the circumferential surface 162 are rounded over to transition to a pair of parallel, spaced apart medial and lateral surfaces 170, 172. An interior of the primary spring 134 is hollow and includes a through orifice extending in the medial-lateral direction. This orifice is partially bound by a pair of parallel, flat walls 176 that are connected at respective ends to an arcuate wall 178. Opposite the arcuate wall 178 is a complementary arcuate wall comprising a first segment 182 spaced apart from a second segment 184 to delineate a slit 186 therebetween. In exemplary form, the slit 186 extends in the medial-lateral direction as well as the proximal-distal direction to provide separation between the housing segments 166, 168.

A proximal end of each housing segment 166, 168 is adjacent a partial opening 190 that extends in the medial-lateral direction and in the anterior-posterior direction (which is perpendicular to the medial-lateral direction and the proximal-distal direction). At the anterior and posterior ends of this opening 190 are a pair of spaced apart walls 194, 196 that delineate an arcuate groove 200 having a concave, U-shaped profile. A distal end of the arcuate groove 200 seamlessly transitions into the longitudinal channel 152. As will be discussed in more detail hereafter, the arcuate groove 200 and longitudinal channel 152 are adapted to receive a portion of the secondary spring 120. Interposing the housing segments 166, 168 and the longitudinal segments 130, 132 is a transition area 210 that maintains the cross-section of the longitudinal channel 152 and also increases an anterior-posterior height to reach the substantially constant anterior-posterior height of the longitudinal segments. In this exemplary embodiment, the transition area 210 includes an arcuate profile where the anterior-posterior height gradually increases to match that of the longitudinal segment attached thereto. As a result, the transition area 210 and the housing segments 166, 168 cooperate to define an internal cavity within which the primary spring 134 is positioned.

Figure 7:
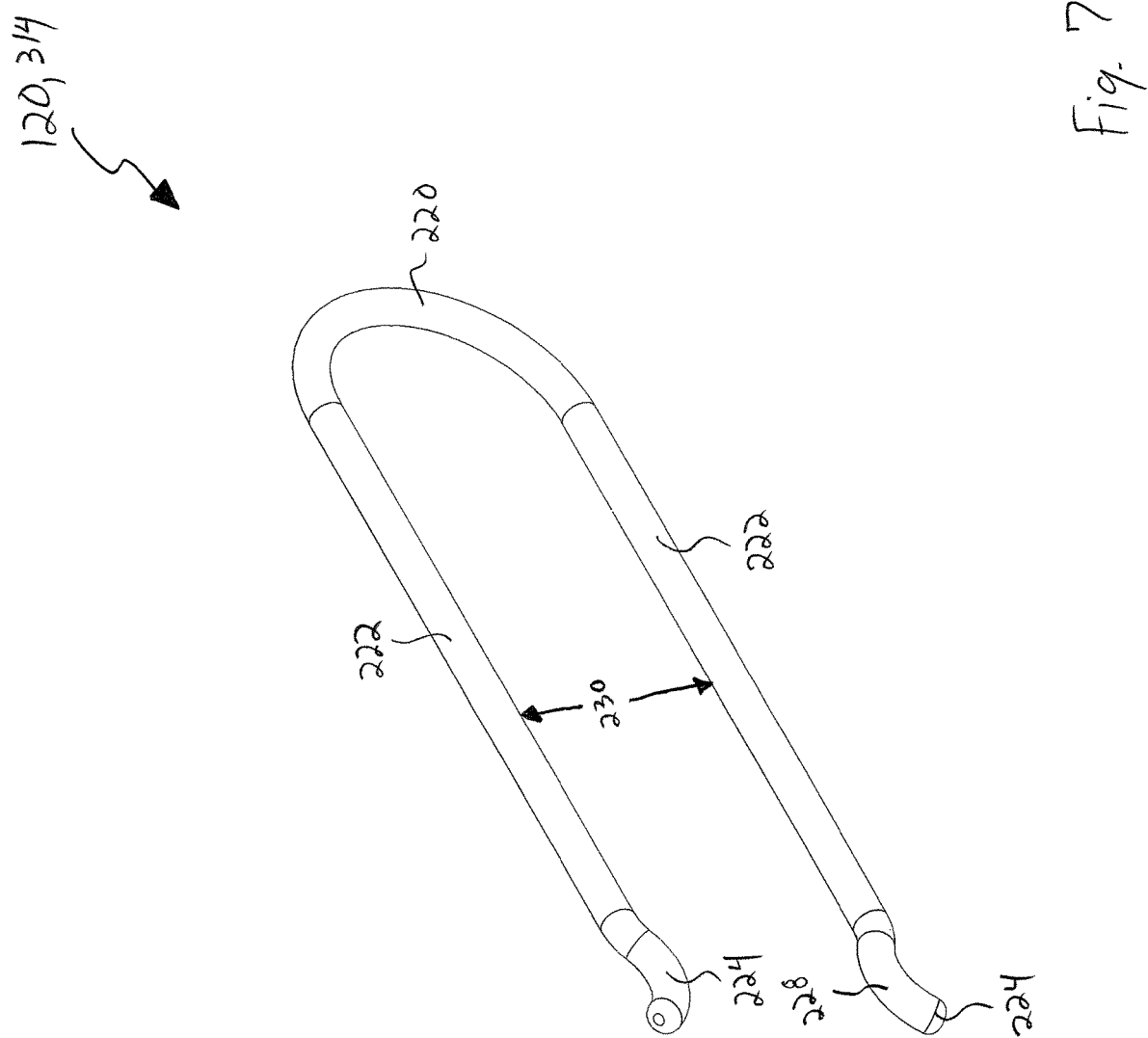
FIG. 7 is an elevated perspective view of an exemplary spring in accordance with the first and second exemplary embodiments.
Figure 8:
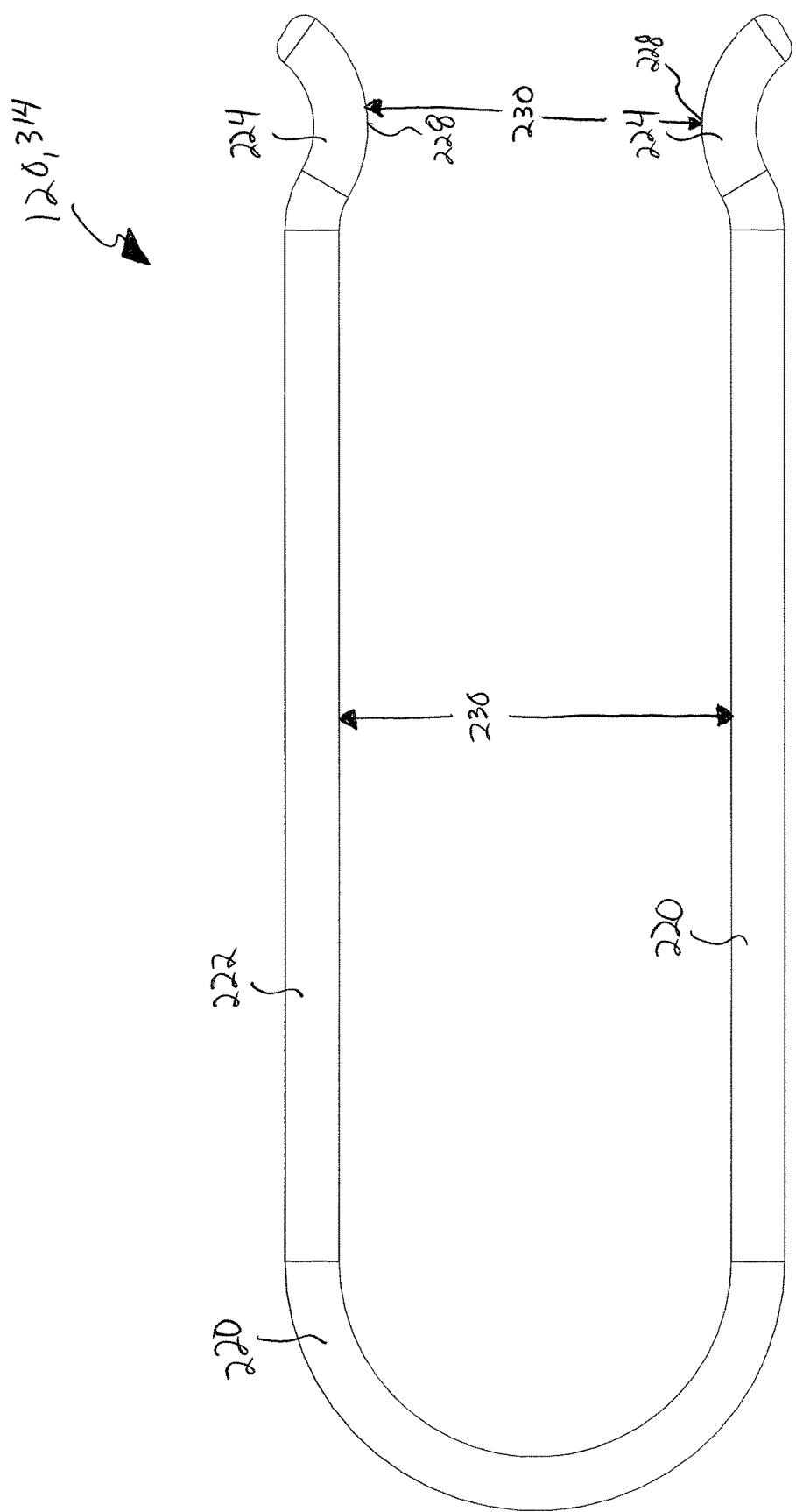
FIG. 8 is a profile view of the exemplary spring of FIG. 7.
Figure 9:
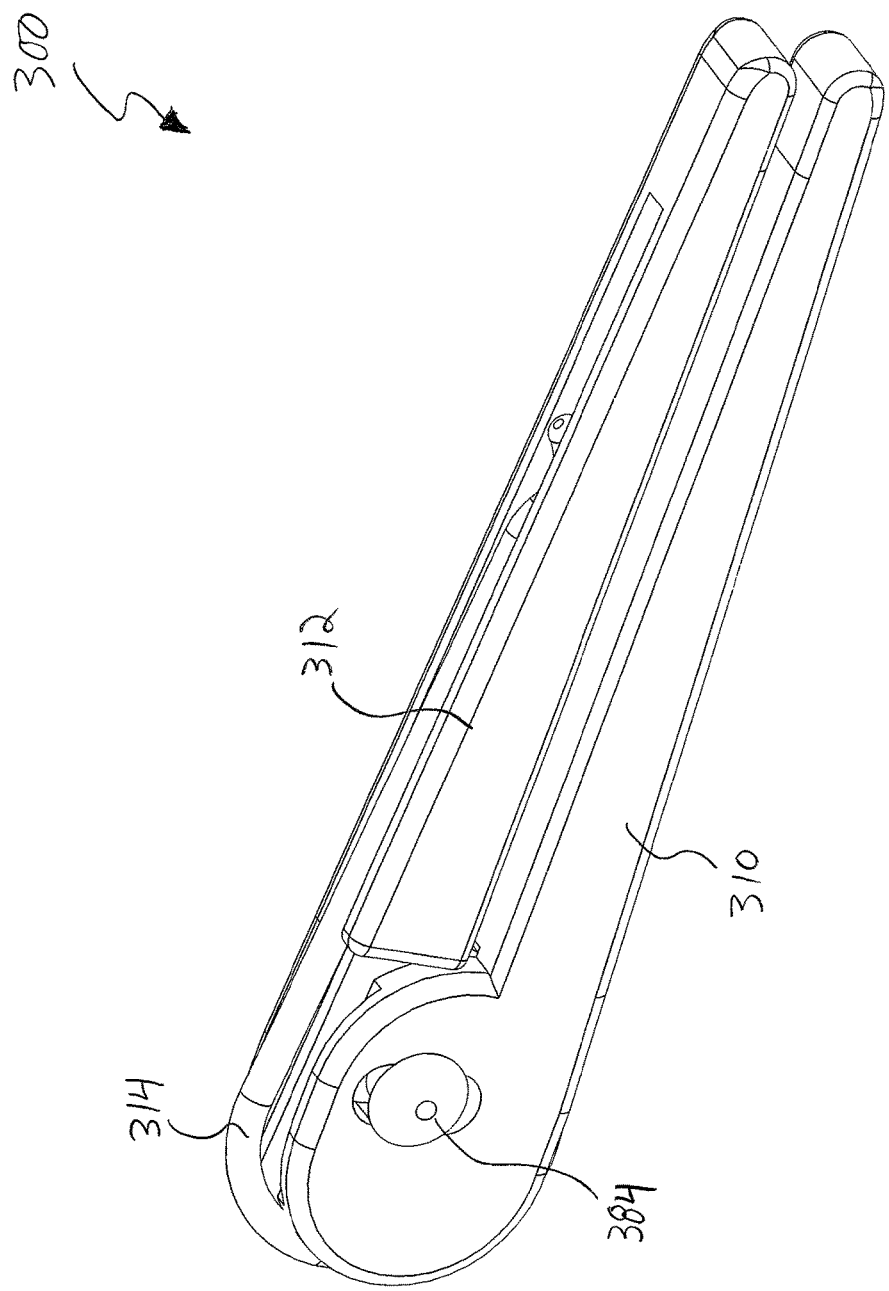
FIG. 9 is an elevated perspective view from the front of a second exemplary occlusion clip in accordance with the instant disclosure.
Figure 10:
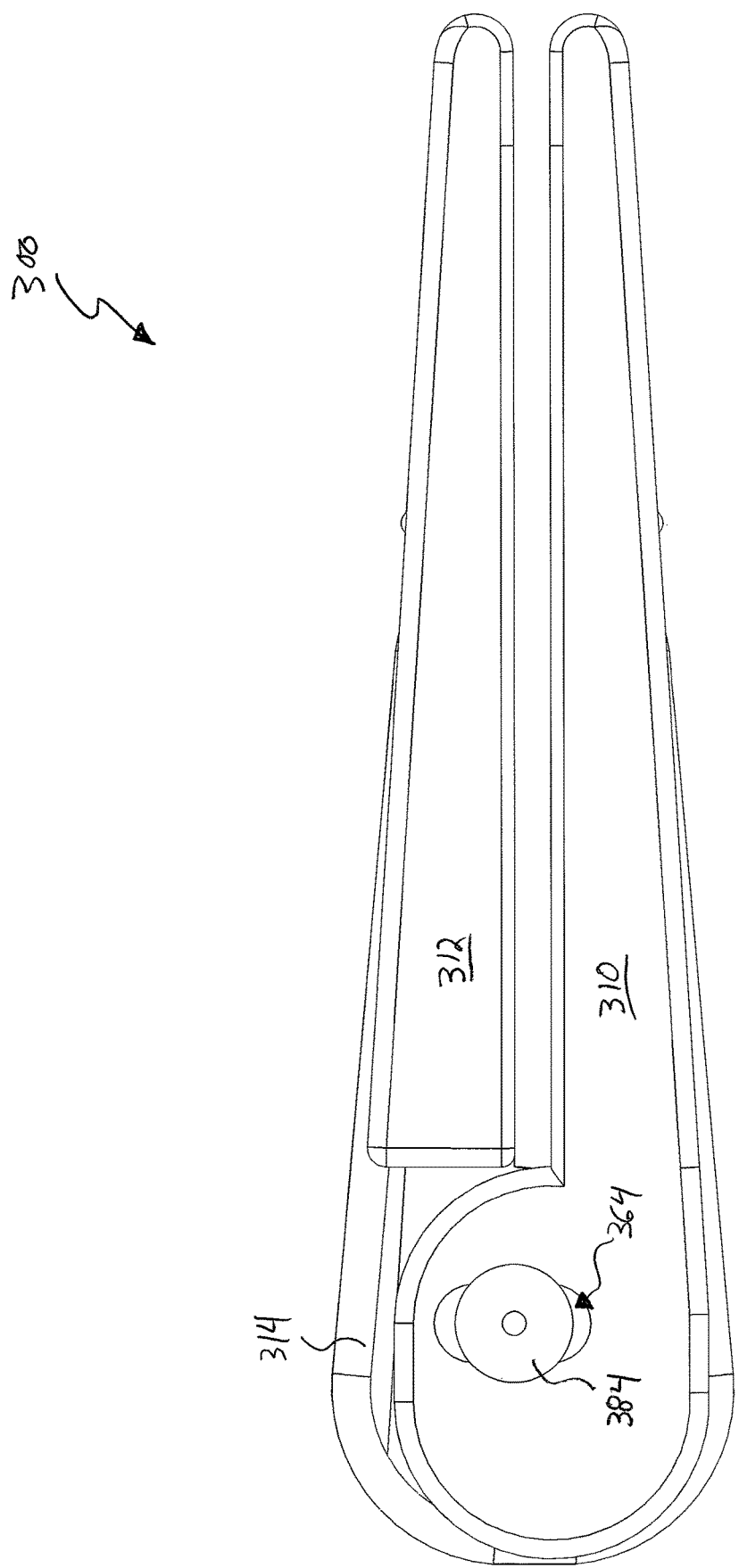
FIG. 10 is a profile view from the front of the second exemplary occlusion clip of FIG. 9.

Referring to FIGS. 7 and 8, an exemplary secondary spring 120 in accordance with the instant disclosure includes a circular cross-section that is generally perpendicular to the longitudinal length thereof, which is the dominant dimension of the secondary spring. While comprising an integrated structure, the secondary spring 120 can be characterized as including three sections, two of which are repeated. A first section 220 is generally U-shaped and includes a substantially constant radial arc to resemble a semi-circle. This first section 220 is integrally formed with a pair of second sections 222 at the distal ends of the first section and a proximal end of each second section. Each of the second sections 222 includes a substantially linear length that extends perpendicularly away from the first section and in parallel to one another and may be biased toward one another to achieve the desired compression force. A distal end of each second section 222 is mounted to a third section 224 that includes a sinusoidal shape. This sinusoidal shape is typified by a convex exterior surface 228 that operates to decrease an anterior-posterior gap 230 that is present along a longitudinal interior of the secondary spring. More specifically, the gap 230 between the second sections 222 is greater than the gap between the third sections 224. As will be discussed in more detail hereafter, the third sections 224 are partially received within a depression formed into the longitudinal segments 130, 132 along a length of the longitudinal channel 152.

Figure 2:
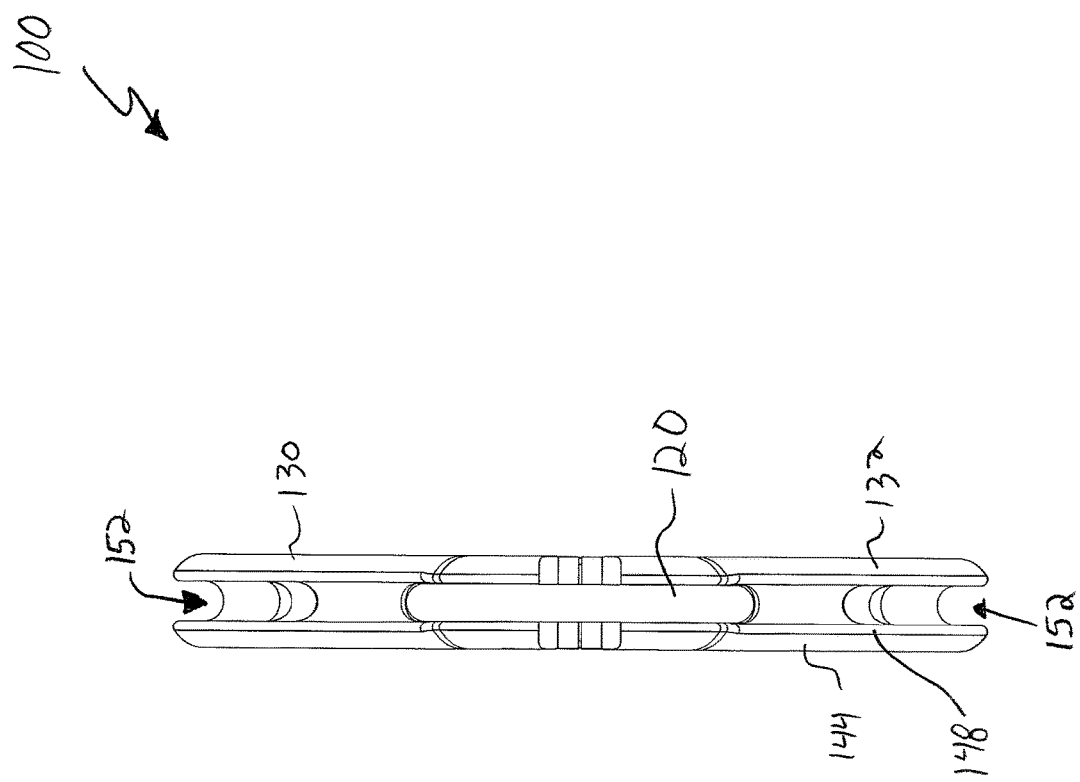
FIG. 2 is a perspective view of the exemplary embodiment of FIG. 1.
Figure 3:
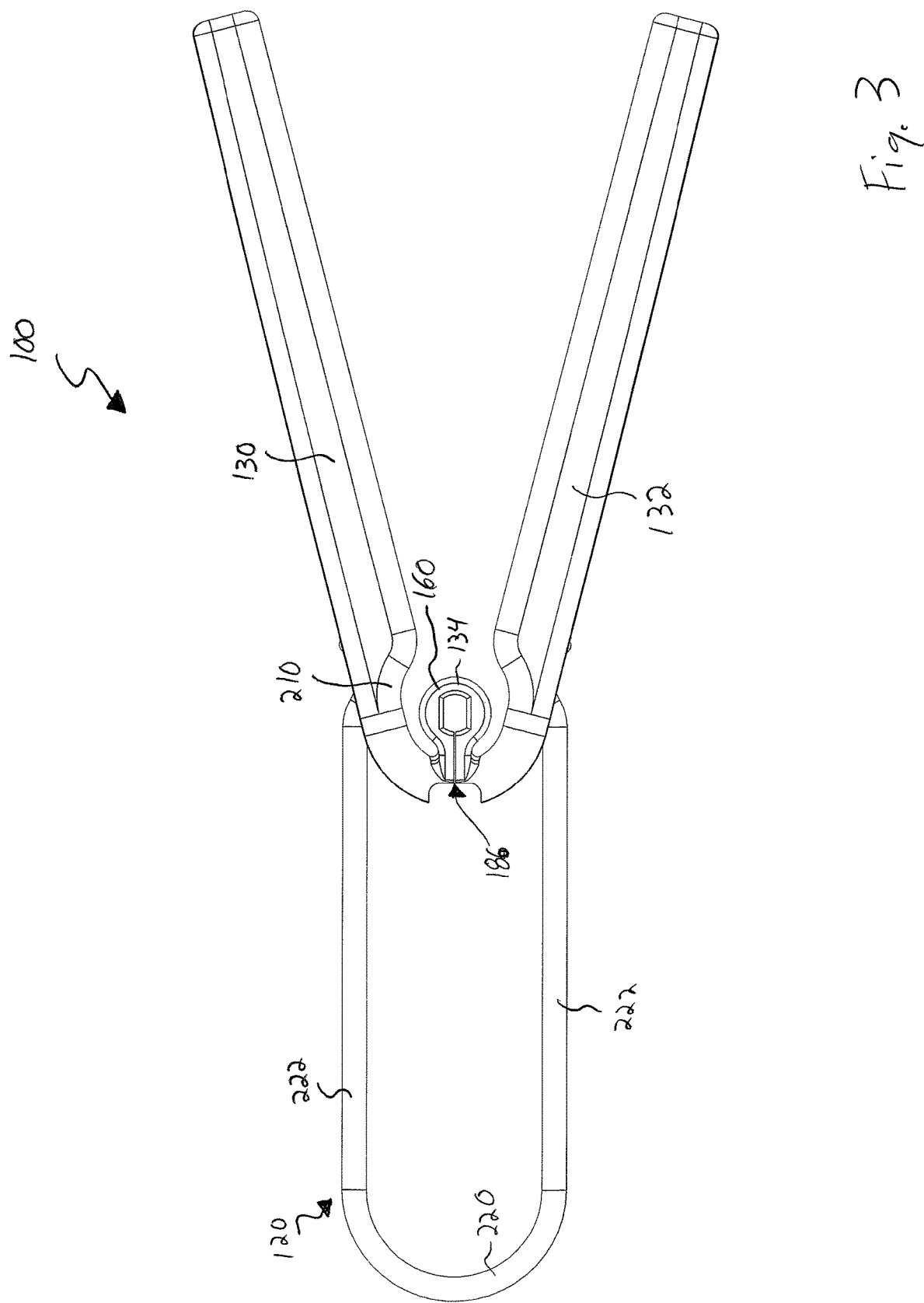
FIG. 3 is a profile view of the exemplary embodiment of FIG. 1.
Figure 4:
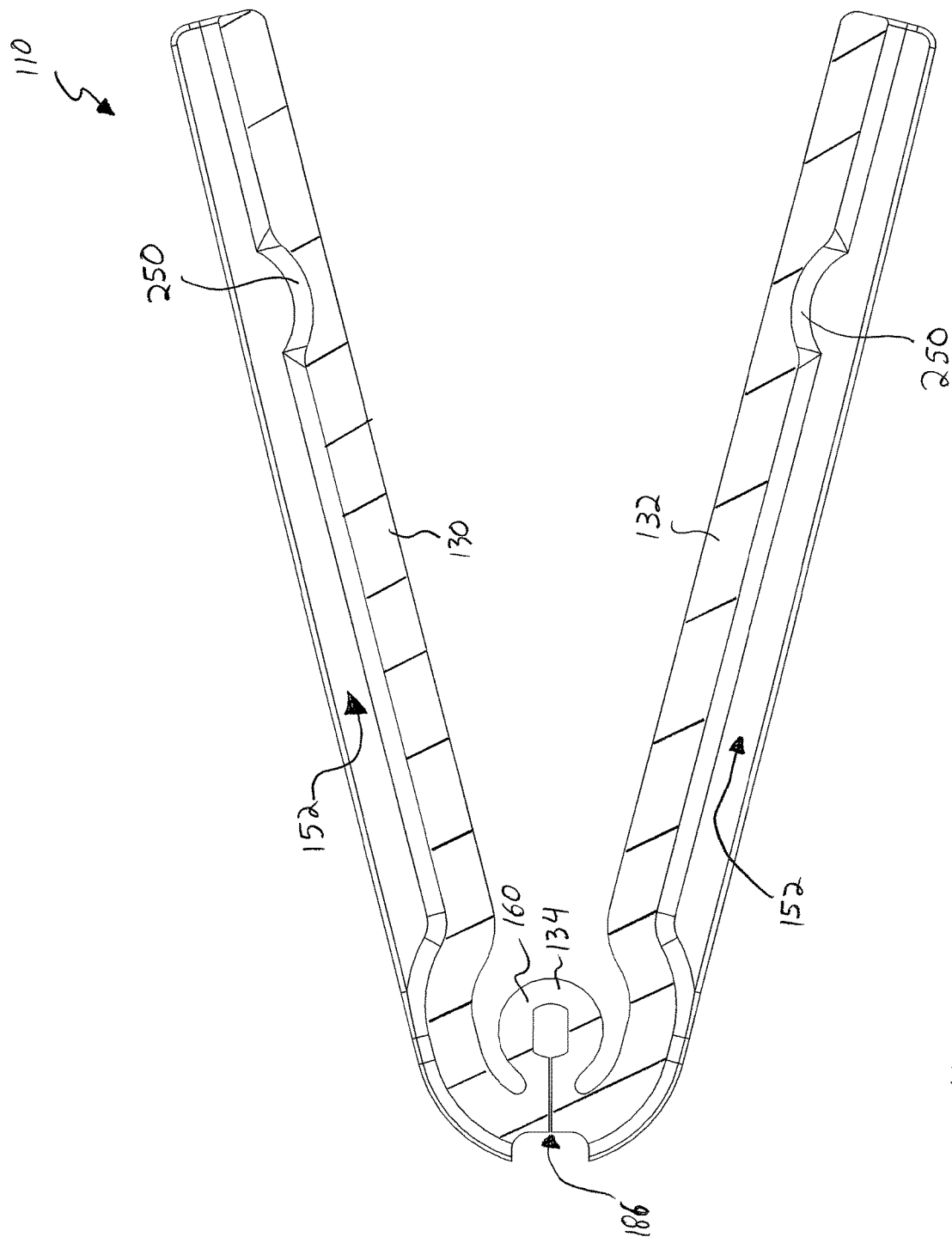
FIG. 4 is a cross-sectional view of the exemplary tongs part of the exemplary embodiment of FIG. 1.
Figure 5:
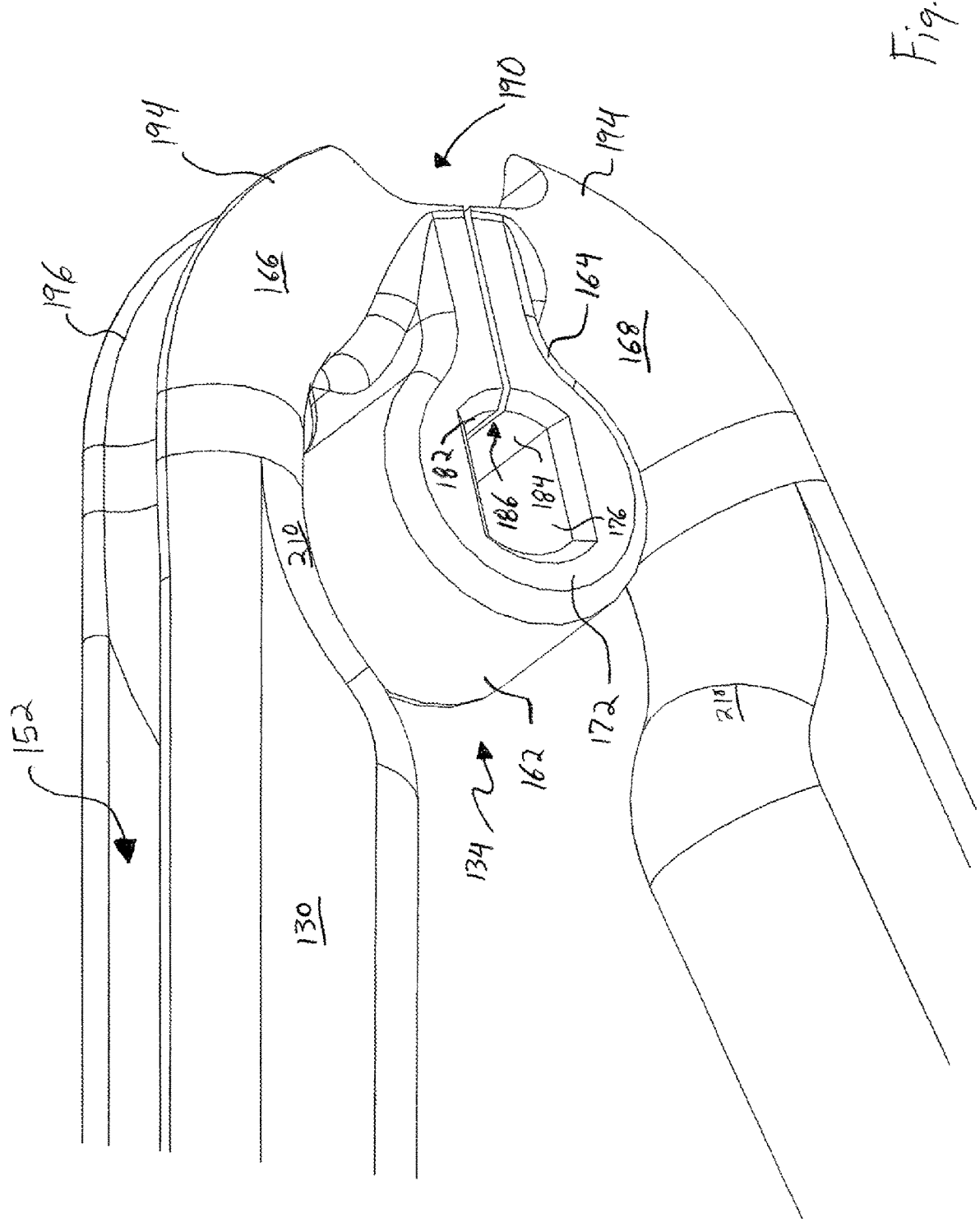
FIG. 5 is an elevated perspective view from a left side of the exemplary primary spring of the exemplary embodiment of FIG. 1.
Figure 6:
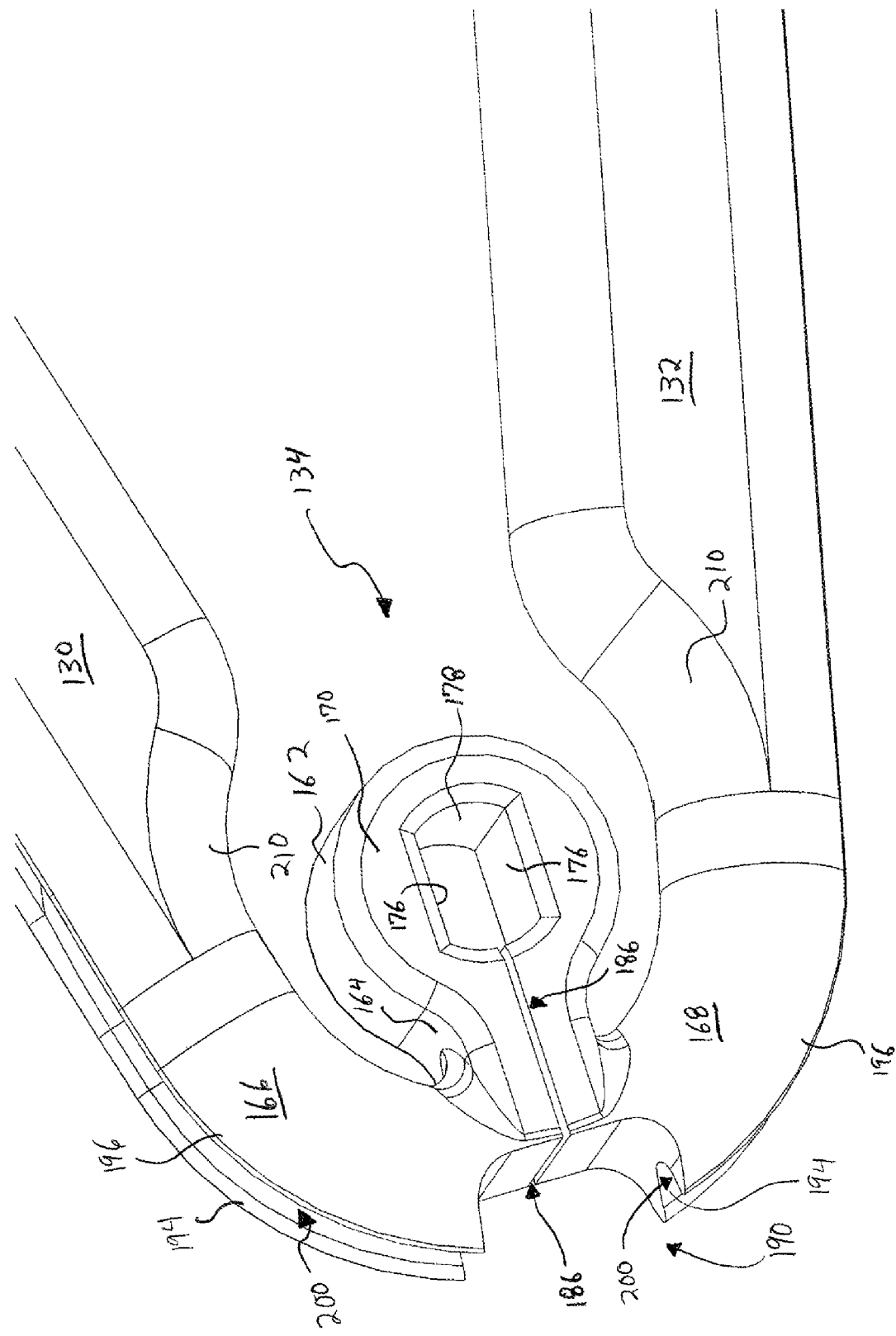
FIG. 6 is an elevated perspective view from a right side of the exemplary primary spring of the exemplary embodiment of FIG. 1.

Referencing FIGS. 1-3, assembly and utilization of the exemplary occlusion clip 100 includes repositioning the tongs 110 so that tissue to be occluded is positioned between the exterior surfaces 140 of the longitudinal segments 130, 132. In exemplary form, the tissue to be occluded may be a human left atrial appendage (not shown).

By way of example, the tongs 110 is positioned so that the longitudinal segments 130, 132 are parallel and compressed against one another to allow the tongs to pass through a trocar. After passing through the trocar and into a mammalian chest cavity, a spacing between distal ends of the longitudinal segments 130, 132 is increased so that the spacing between the segments is large enough to accommodate a left atrial appendage of a heart.

After the tissue in question, in this case the left atrial appendage, is positioned between the longitudinal segments 130, 132, the longitudinal segments are moved closer to one another. This may be accomplished by manually compressing the longitudinal segments 130, 132 toward one another or by using the secondary spring 120 to move the longitudinal segments toward one another. For purposes of discussion, it will be presumed that that secondary spring 120 is utilized to compress the longitudinal segments 130, 132 toward one another.

In order to use the secondary spring 120 to compress the longitudinal segments toward one another, the secondary spring is inserted through the trocar and into alignment with the tongs, presuming this alignment is not already completed. More specifically, the third sections 224 of the secondary spring 120 are aligned with the proximal end of the tongs 110 so that each of the third sections is at least partially received within a corresponding arcuate groove 200. At this time, the secondary spring 120 is repositioned in the distal direction with respect to the tongs 110 so that the convex exterior surface 228 contacts the surface delineating the arcuate groove 200. Continued movement of the secondary spring 120 toward the distal end of the tongs 110 causes the third sections 224 to increase the gap 230 therebetween to accommodate the tongs. The resilient nature of the secondary spring 120, resulting from an increase in the gap 230, exerts a bias force that causes the longitudinal segments 130, 132 to be compressed toward one another. Even further movement of the secondary spring 120 toward the distal end of the tongs 110 causes the spacing between the longitudinal segments 130, 132 to decrease and compress the segments against the tissue in question, in this case the left atrial appendage. The further along the secondary spring moves distally with respect to the tongs 110, the greater the moment that is exerted against the longitudinal members 130, 132 because the moment necessary to move the second sections 222 apart increases as one moves closer to the first section 220. Eventually, movement of the secondary spring 120 toward the distal end of the tongs 110 reaches a point where both third sections 224 are received within secondary depressions 250 formed deeper into the longitudinal segments 130, 132 as part of the longitudinal channels 152.

Figure 20:
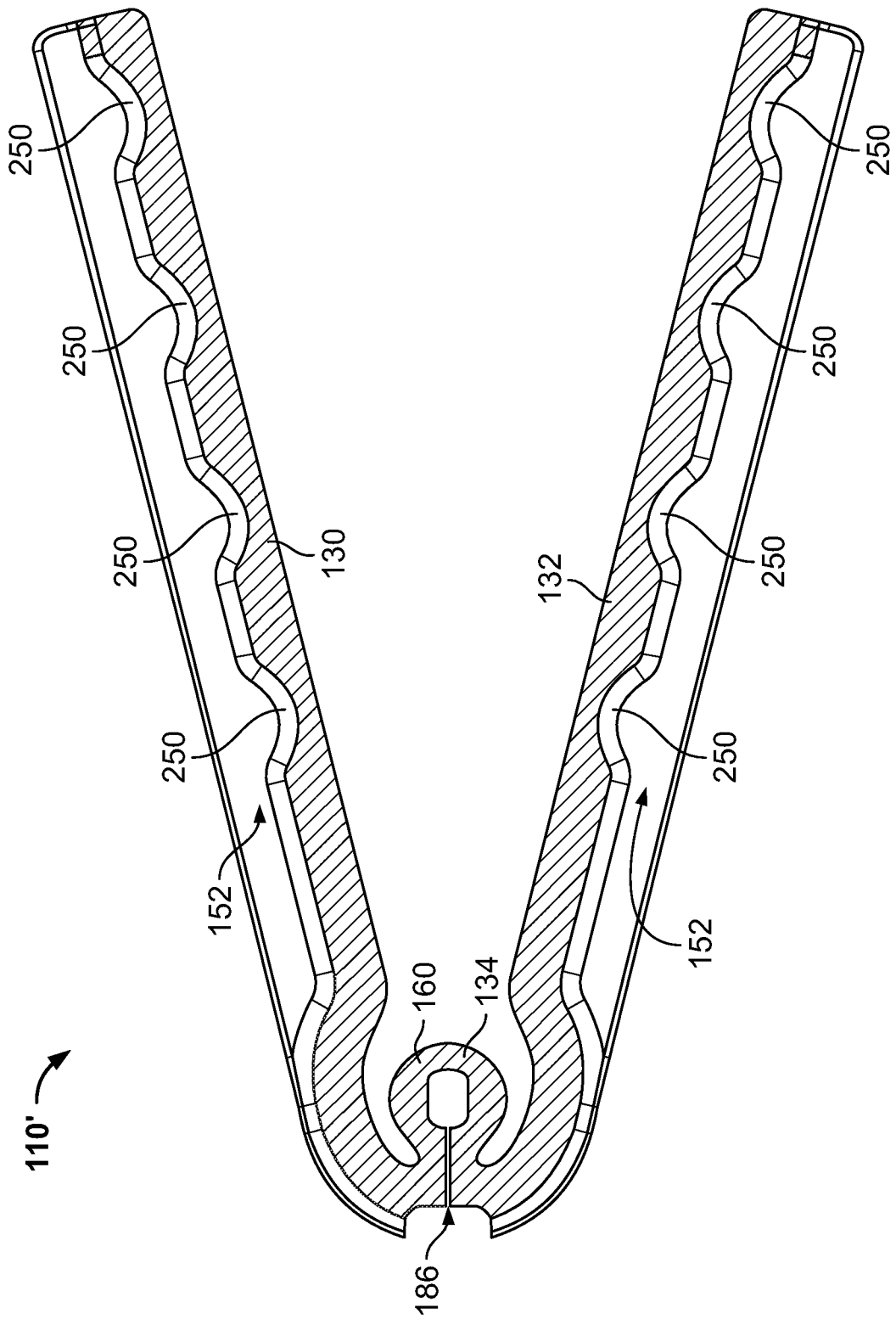
FIG. 20 is a cross-sectional view of a first alternate exemplary tongs in accordance with the instant disclosure.
Figure 21:
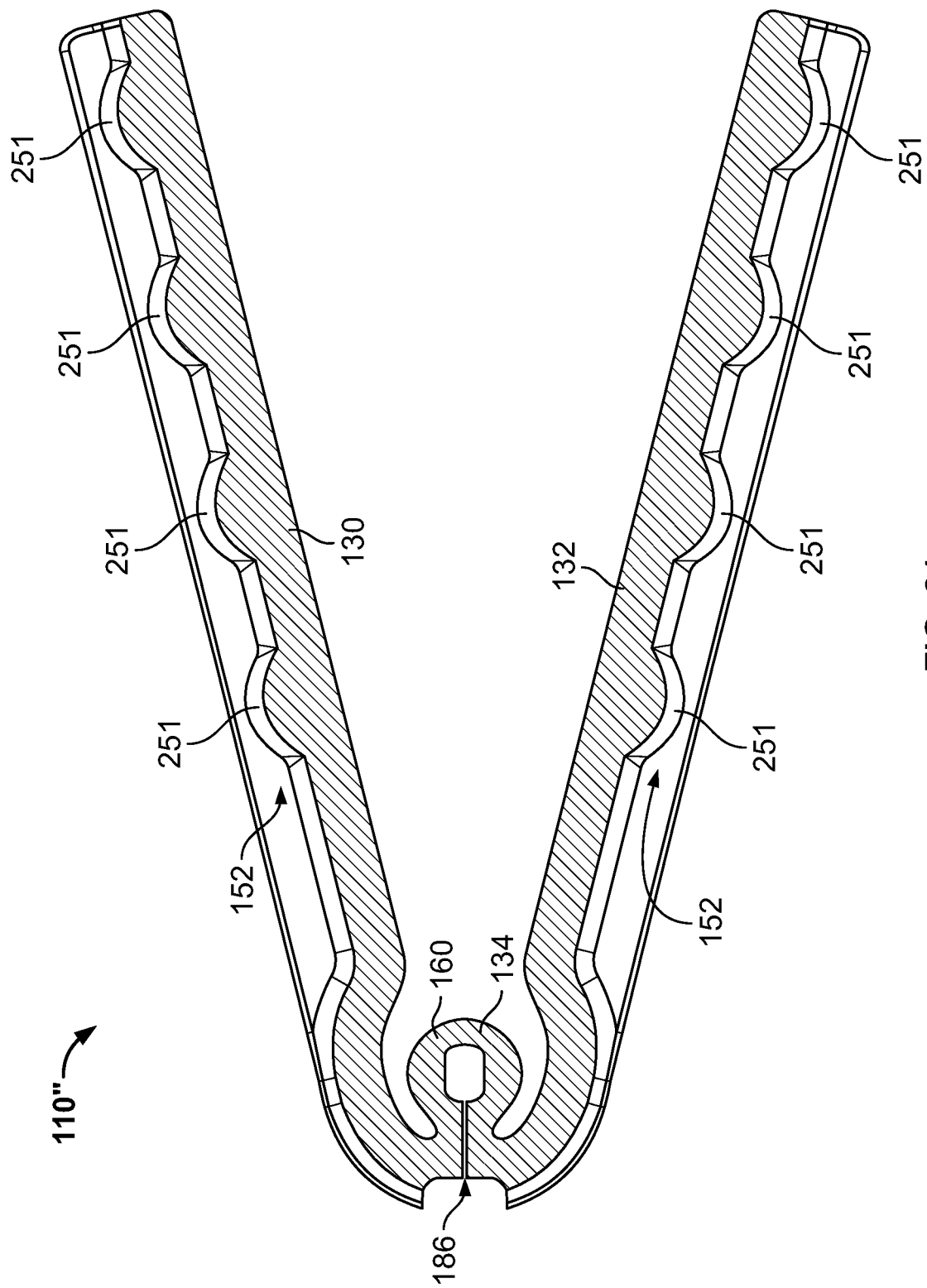
FIG. 21 is a cross-sectional view of a second alternate exemplary tongs in accordance with the instant disclosure.
Figure 22:
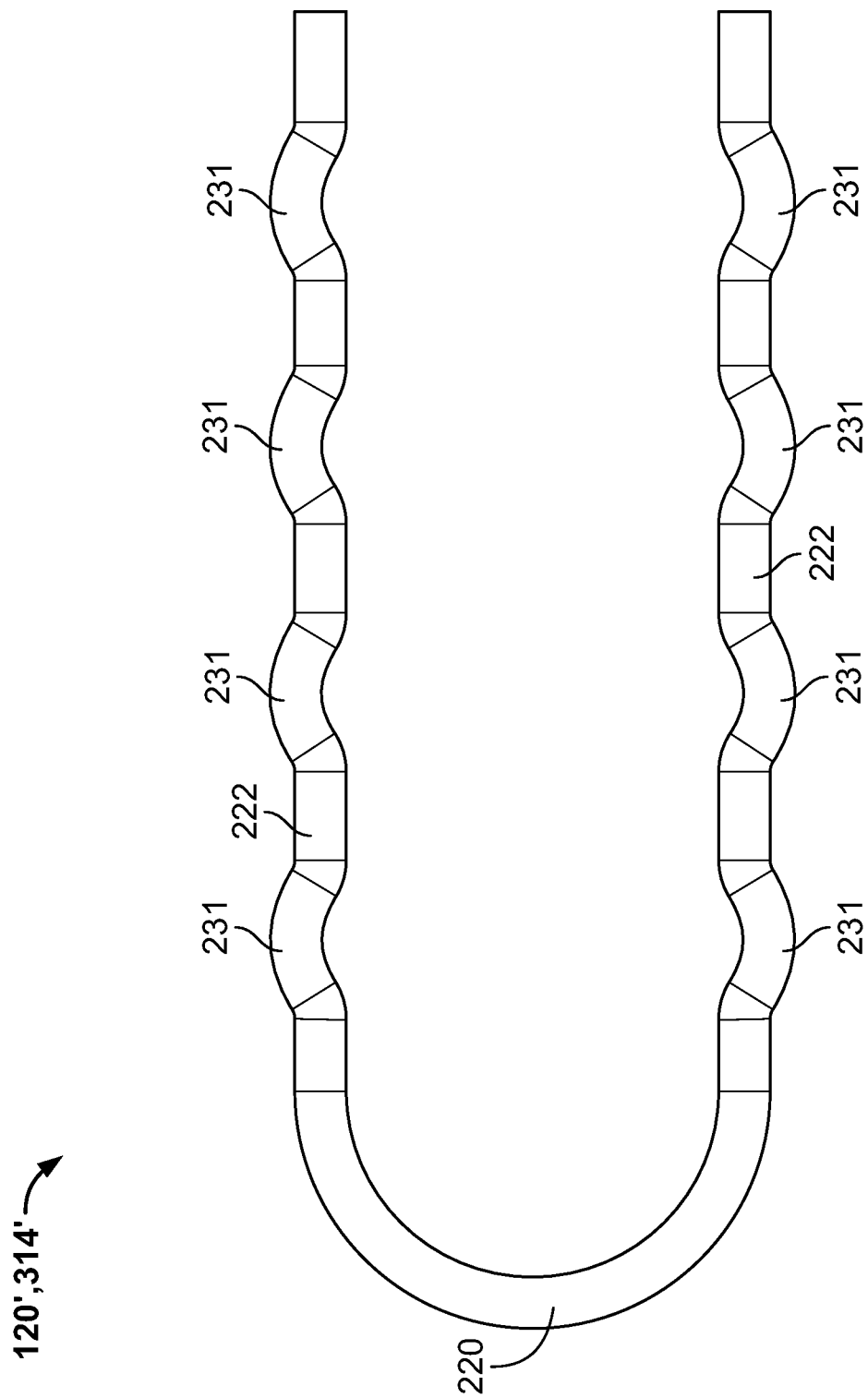
FIG. 22 is a profile view of a first alternate exemplary spring in accordance with the instant disclosure.
Figure 23:
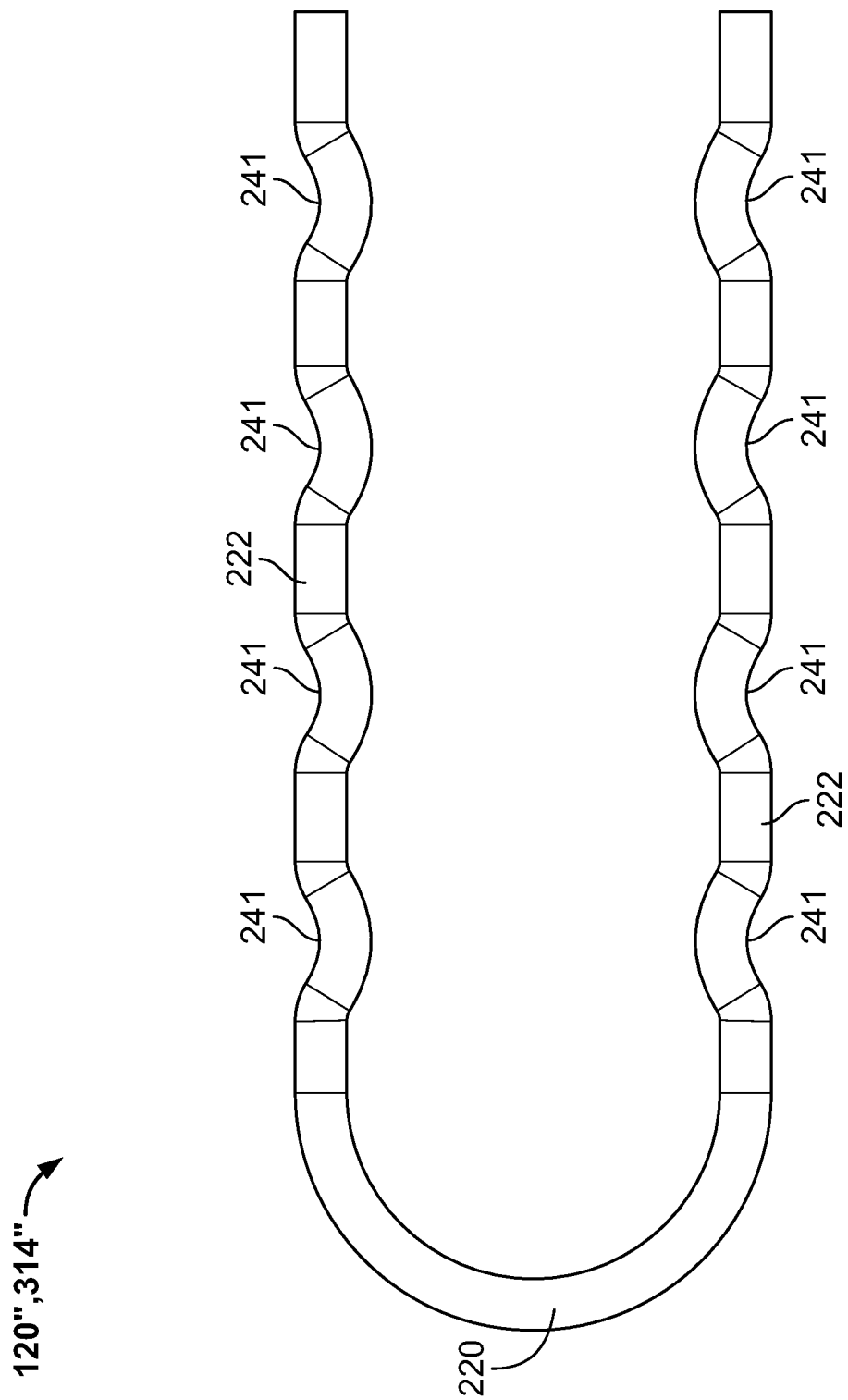
FIG. 23 is a profile view of a second alternate exemplary spring in accordance with the instant disclosure.

It should be noted that while the exemplary embodiment includes a single secondary depression 250 for each of the longitudinal members 130, 132, it is also within the scope of the disclosure to provide multiple secondary depressions 250 longitudinally distributed along the longitudinal members in order to accommodate ranges of force balancing, such as the alternate exemplary tongs 110' depicted in FIG. 20. Likewise, while the exemplary secondary spring 120 has been shown to include a pair of third sections 224, one adapted to engage each longitudinal member 130, 132, it is also within the scope of the disclosure for a second alternate secondary spring 120", 314", such as depicted in FIG. 23, to include multiple projections 241 in series and/or spaced apart from one another to engage one or more of the secondary depressions 250 of each longitudinal member of the alternate exemplary tongs 110'. Conversely, it is also within the scope of the disclosure to provide multiple secondary depressions 231 longitudinally distributed along the longitudinal members, such as shown in FIG. 22, in order to accommodate ranges of force balancing, such as the second exemplary tongs 110" depicted in FIG. 21 that include a plurality of secondary projections 251 distributed along each longitudinal member.

When the secondary depressions 250 receive the third sections 224 of the secondary spring 120, the secondary spring 120 is relatively locked into a longitudinal friction fit with respect to the tongs 110. Likewise, when the secondary depressions 250 receive the third sections 224 of the secondary spring 120, a bias exerted upon the longitudinal segments 130, 132 is approximately equal along the longitudinal length thereof. This longitudinal bias is operate to occlude the tissue clamped between the longitudinal segments 130, 132 and is the cooperative product of the bias of the secondary spring 120 and the bias of the primary spring 134. More specifically, the secondary spring 120 may be selected based upon the bias it exerts to match that of the primary spring 134. Conversely, the primary spring 134 may be designed to include a bias that matches that of a predetermined secondary spring 120.

Disassembly of the exemplary occlusion clip 100 includes repositioning the secondary spring 120 proximally with respect to the tongs 110 so that the third sections 224 become displaced from the depressions 250. Eventually, continued proximal movement of the secondary spring 120 with respect to the tongs 110 results in the third sections 224 passing beyond the proximal most portion of the tongs, resulting in complete disengagement between the tongs and secondary spring.

While the foregoing exemplary secondary spring 120 has been shown and described as having a uniform, circular cross-section along the longitudinal length thereof, it is also within the scope of this disclosure to provide differing cross-sections. By way of example, the cross-section of the secondary spring 120 may take on a rectangular shape having a dominant dimension that makes distortion in a first plane more difficult that distortion in a second plane, perpendicular to the first plane, typified by a subordinate dimension. Moreover, the cross-section of the secondary spring 120 may change along its longitudinal length. By way of example, a circular cross-section may be exhibited by a portion of the secondary spring, followed by a non-circular cross section (e.g., an oblong shape, rectangular shape, or otherwise). In other words, the cross-section along the length of the secondary spring may have a portion that is configured to retard motion or more readily allow motion in one or more directions, followed by or proceeded by a portion having a different cross-section that is configured to retard motion or more readily allow motion in one or more of the same or different directions. By way of further example, the U-shaped proximal first section 220 of the secondary spring 120 may have a circular cross-section, while the second sections 222 may have a rectangular profile with a dominant dimension in the lateral direction to allow greater deflection up or down rather than side to side. These different cross-sections may be useful to balance forces applied by the longitudinal segments 130, 132.

Referring to FIGS. 7-17, a second exemplary occlusion clip 300 includes a first jaw 310 repositionably mounted to a second jaw 312 and adapted to be biased toward one another using a secondary spring 314. In this exemplary embodiment, the jaws 310, 312 are fabricated from a resilient or partially resilient material such as, without limitation, a biologic material, a biologically reabsorbable material, a plastic, a metal, a metal alloy, and carbon fiber. In further exemplary form, the material may be formulated, include additives, or naturally be reabsorbable by a mammalian body within a predetermined period of time, such as six months or longer.

The spring 314 is also fabricated from a resilient material. Exemplary materials used to fabricate the spring 314 include, without limitation, a biologic material, a biologically reabsorbable material, a plastic, a metal, a metal alloy, and carbon fiber.

Figure 11:
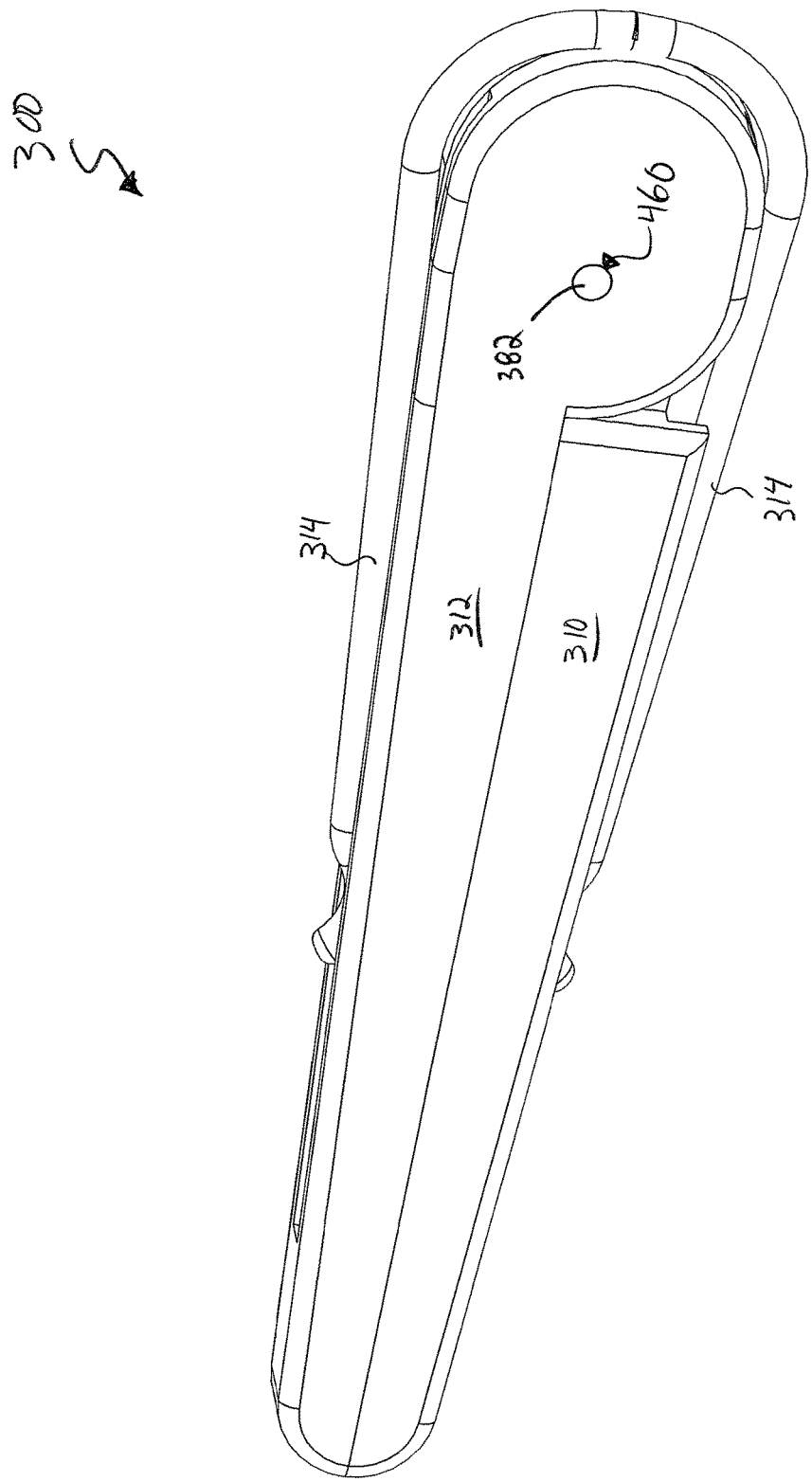
FIG. 11 is an elevated perspective view from the rear of the second exemplary occlusion clip of FIG. 9.
Figure 12:
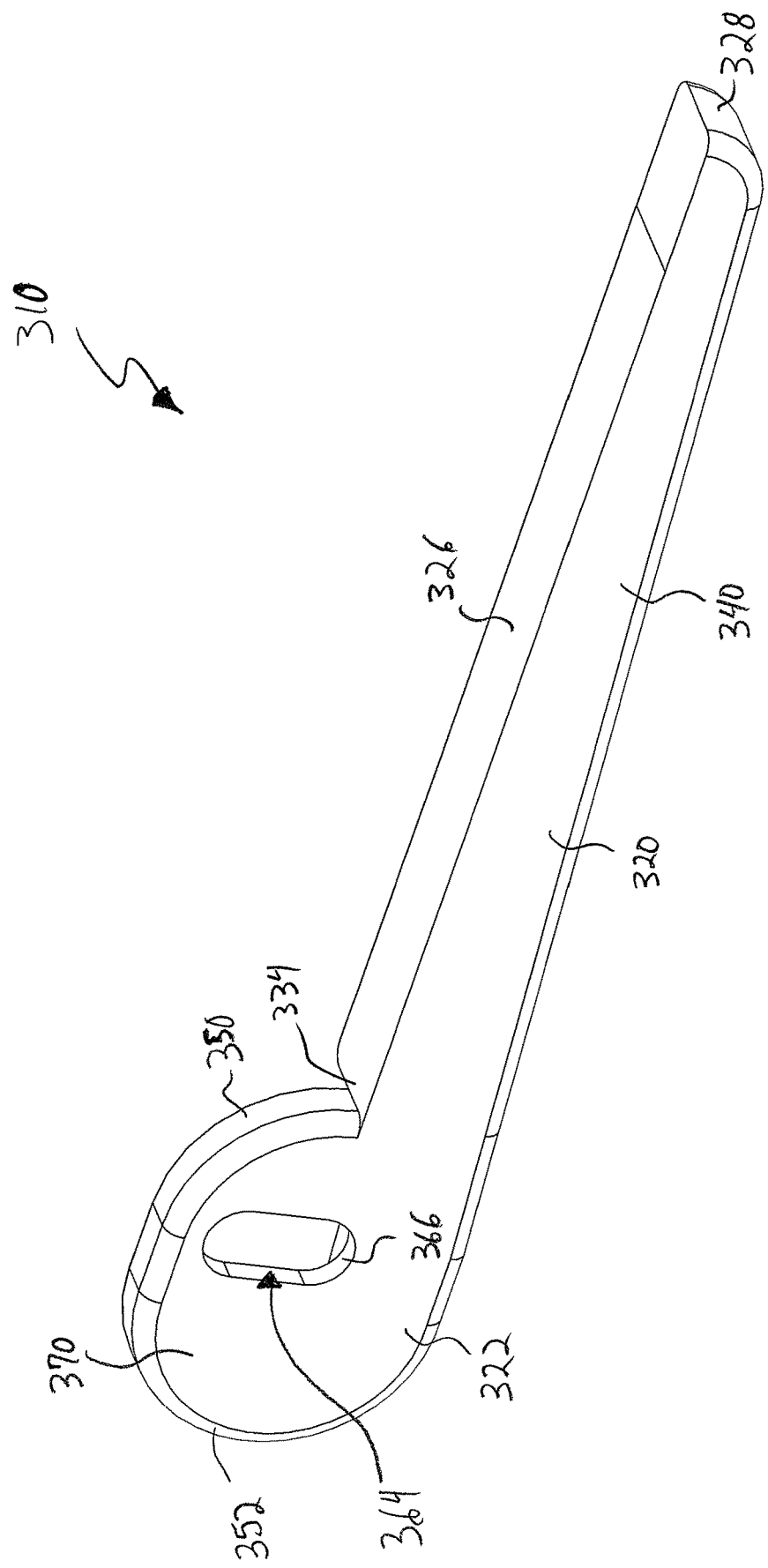
FIG. 12 is an elevated perspective view from the front of a first jaw of the second exemplary occlusion clip of FIG. 9.
Figure 13:
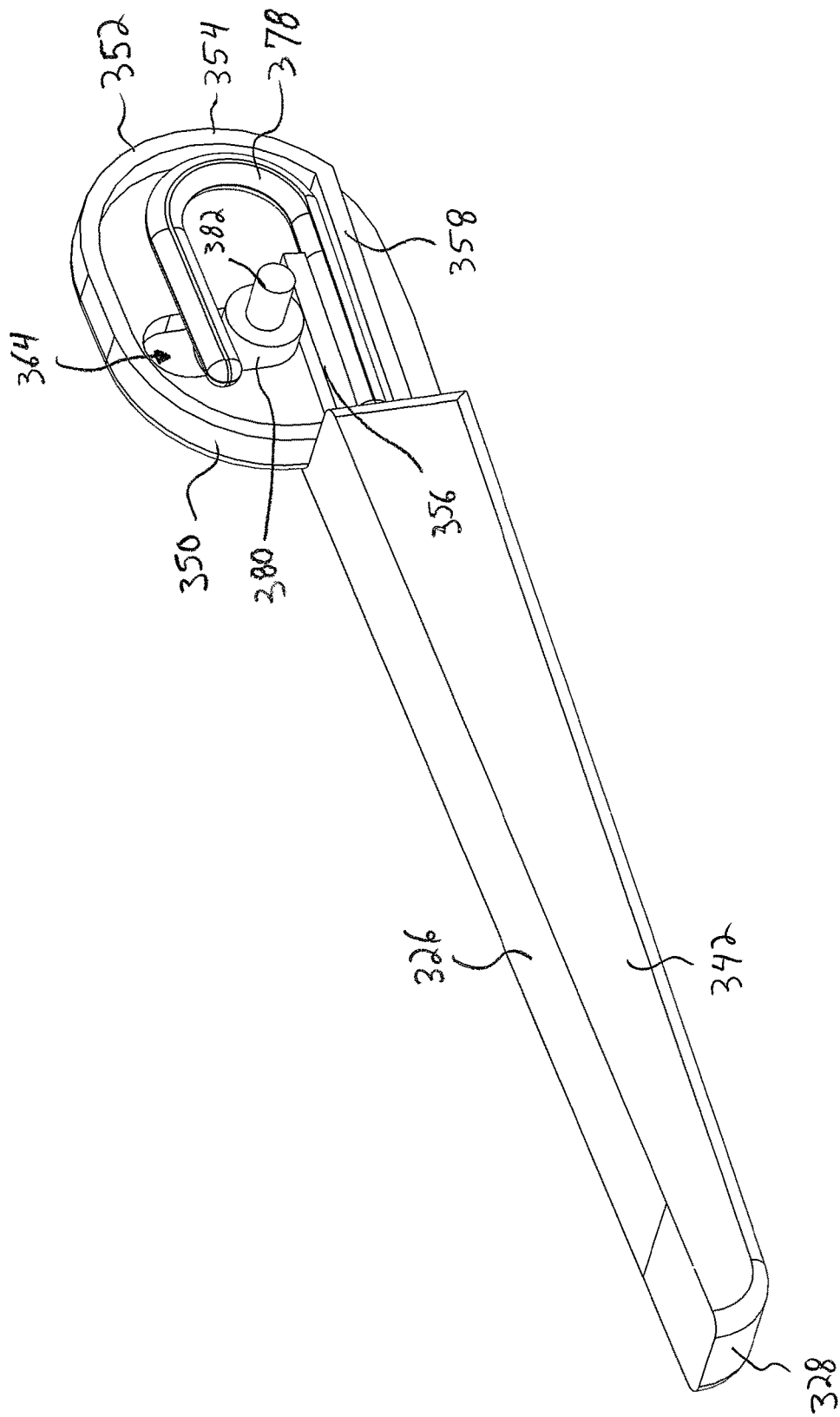
FIG. 13 is an elevated perspective view from the rear of the first jaw of the second exemplary occlusion clip of FIG. 9, shown with a first secondary spring and pin mounted to the first jaw.
Figure 14:
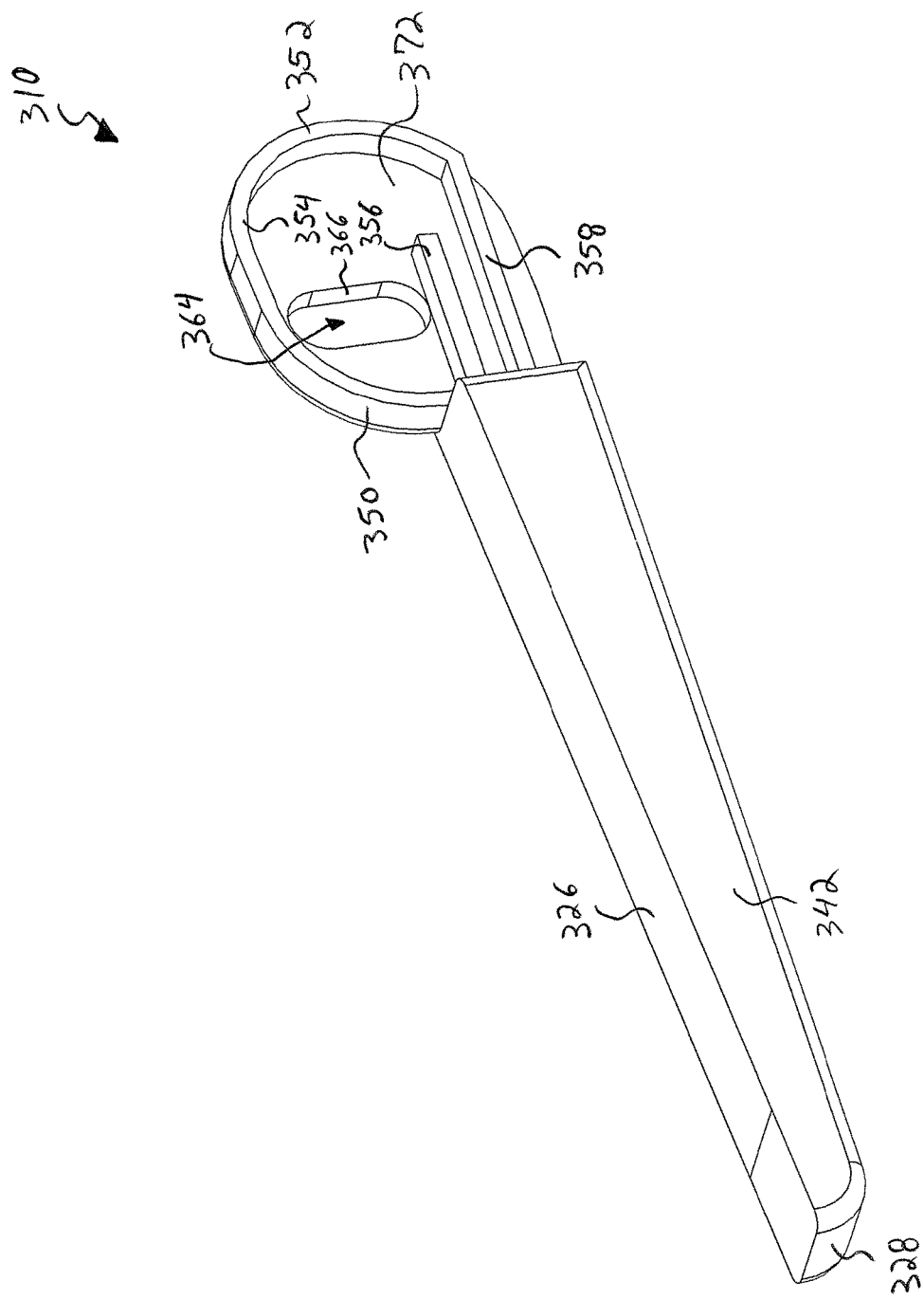
FIG. 14 is an elevated perspective view from the rear of the first jaw of the second exemplary occlusion clip of FIG. 9.
Figure 15:
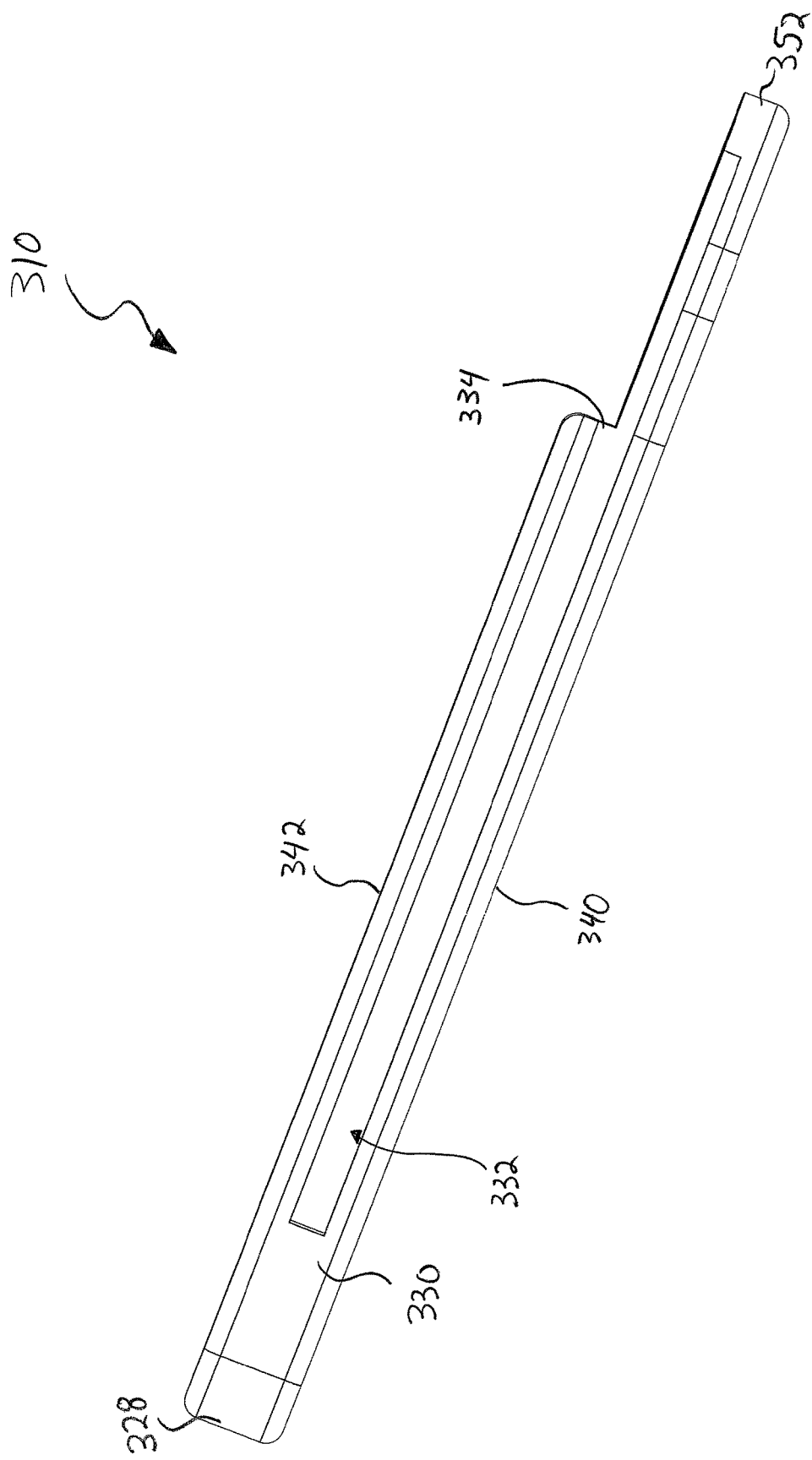
FIG. 15 is a bottom view of the first jaw of the second exemplary occlusion clip of FIG. 9.

Referring to FIGS. 11-13, the first jaw 310 includes an elongated platform 320 that extends from a hub 322. The elongated platform 320 comprises an inclined occlusion surface 326 that is substantially planar but causes the height of the platform to gradually increase from a distal tip 328 to a proximal ending 334. Opposite the inclined surface is a bottom surface 330 having formed therein a longitudinal trench 332 having a substantially rectangular cross-section that extends partially beyond the proximal ending 334. It should be noted that the longitudinal trench 332 may have a cross-section other than rectangular including, without limitation, oblong and semicircular. The distal tip 328 interposes the inclined surface 326 and the bottom surface 330, along with a pair of spaced apart, planar lateral surfaces 340, 342. The planar lateral surfaces 340, 342 are each generally perpendicular to the inclined surface 326 and the bottom surface 330.

The hub 322 is located proximate the elongated platform 320 and is laterally inset with respect to one of the lateral surfaces 342, but flush with respect to the other lateral surface 340. A distal portion 350 of the hub 322 includes an arcuate profile from distal to proximal and rounds over at a proximal portion 352. The distal and proximal portions 350, 352 include a peripheral flange 354 having a pair of parallel, linear segments 356, 358 extending into the interior of the hub 322. Just above the first linear segment 356 is an oblong through opening 364 delineated by an oblong interior wall 366. More specifically, the opening 364 extends through a wall having a pair of parallel, lateral surfaces 370, 372. In particular, the first lateral surface 370 is co-planar with the lateral surface 340 of the elongated platform 320.

A primary spring 378 is received within the interior of the hub 322 and configured to provide bias for a proximal end of the exemplary occlusion clip 300. More specifically, a cylindrical pin 380 extends through the oblong opening 364 and into the interior of the hub 322, where a smaller diameter portion 382 of the cylindrical pin is adapted to be received within a through hole of the second jaw 312. A lower portion of the cylindrical pin 380 is bounded by the first linear segment 356, while an upper portion of the cylindrical pin is bounded by the primary spring 378. In this manner, the cylindrical pin 380 is able to move vertically within the oblong opening 364, but to do so the bias of the primary spring 378 must be overcome. In this exemplary embodiment, the primary spring 378 comprises a simple U-shaped configuration and where one of the ends of the spring is received between the linear segments 356, 358, while the arcuate portion of the secondary spring abuts the peripheral flange 354. In this manner, the primary spring 378 is relatively stationary, but may be deformed to allow the cylindrical pin 380 to vertically travel within the oblong opening 364, thereby allowing a proximal spacing between the jaws 310, 312 to be changed.

Figure 16:
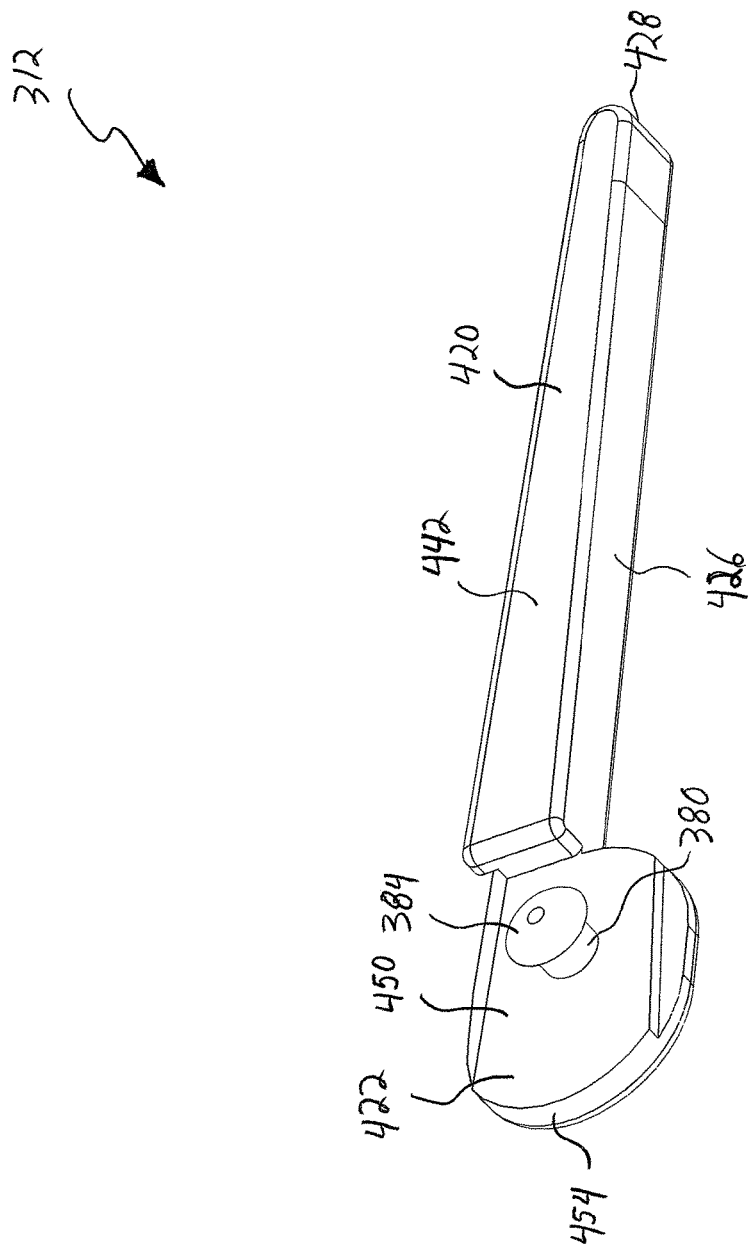
FIG. 16 is a bottom perspective view from the front of a second jaw of the second exemplary occlusion clip of FIG. 9.
Figure 17:
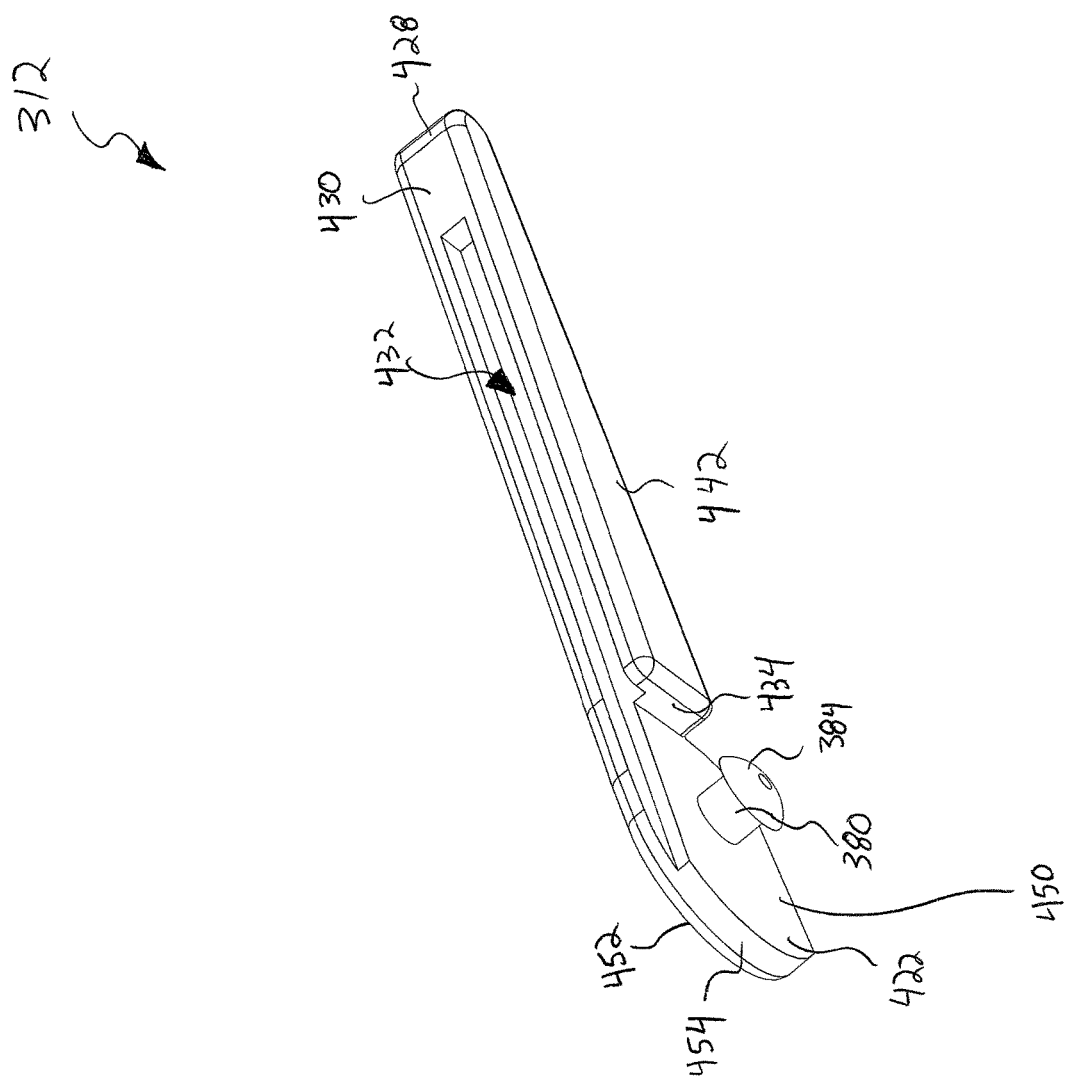
FIG. 17 is an elevated perspective view from the front of the second jaw of the second exemplary occlusion clip of FIG. 9.

Referring to FIGS. 16 and 17, the second jaw 312 includes an elongated platform 420 that extends from a solid hub 422. The elongated platform 420 comprises an inclined occlusion surface 426 that is substantially planar but causes the height of the platform to gradually increase from a distal tip 428 to a proximal ending 434. Opposite the inclined surface is a bottom surface 430 having formed therein a longitudinal trench 432 having a substantially rectangular cross-section that extends partially beyond the proximal ending 434. It should be noted that the longitudinal trench 432 may have a cross-section other than rectangular including, without limitation, oblong and semicircular. The distal tip 428 interposes the inclined surface 426 and the bottom surface 430, along with a pair of spaced apart, planar lateral surfaces 440, 442. The planar lateral surfaces 440, 442 are each generally perpendicular to the inclined surface 426 and the bottom surface 430.

The solid hub 422 comprises a pair parallel, spaced apart lateral surfaces 450, 452 that are bounded by an arcuate circumferential surface 454. In this exemplary embodiment, the interior lateral surface 450 includes an orifice 460 (see FIG. 11) that receives the smaller diameter portion 382 of the cylindrical pin 380 via a friction fit, thereby joining the jaws to one another. In this exemplary embodiment, the cylindrical pin 380 includes an oversized head 384 that provides a boundary for the first jaw 310 in order to allow the jaws 310, 312 to move with respect to one another, but inhibit lateral disengagement between the jaws where the jaws might otherwise come apart.

In this exemplary embodiment, the secondary spring 314 includes generally the same structure and shape as the secondary spring 120 of the first exemplary embodiment, which is shown in FIGS. 7 and 8. Accordingly, description of the spring 314 has been omitted in this exemplary embodiment in furtherance of brevity.

Referring back to FIGS. 9-17, assembly and utilization of the exemplary occlusion clip 300 includes repositioning the jaws 310, 312 so that tissue to be occluded is positioned between the inclined surfaces 326 of the elongated platforms 320. In exemplary form, the tissue to be occluded may be a human left atrial appendage (not shown).

By way of example, the jaws 310, 312 are positioned so that the inclined surfaces 326 of the elongated platforms 320 are parallel and compressed against one another to allow the jaws to pass through a trocar. After passing through the trocar and into a mammalian chest cavity, a spacing between the inclined surfaces 326 of the elongated platforms 320 is increased by overcoming the bias of the primary spring 378 in order to vertically reposition the second jaw 312 with respect to the first jaw 310 so that the pin 380 is against an uppermost portion of the oblong interior wall 366 so that the spacing therebetween is large enough to accommodate a left atrial appendage of a heart.

After the tissue in question, in this case the left atrial appendage, is positioned between the inclined surfaces 326 of the elongated platforms 320, the elongated platforms are allowed to move closer to one another, in part by discontinuing to overcome the bias of the primary spring 378. In addition, additional bias is applied to the jaws 310, 312 by mounting the spring 314 to the jaws so the elongated platforms 320, 420 are compressed toward one another.

In order to use the spring 314 to compress the inclined surfaces 326, 426 of the elongated platforms 320, 420 toward one another, the spring is first inserted through the trocar and into alignment with the jaws 310, 312, presuming the spring is not already in alignment with the elongated platforms. More specifically, the third sections 224 of the spring 314 are aligned with the longitudinal trenches 332, 432 so that the third sections contact the hubs 322, 422 of both jaws 310, 312. Further movement of the spring 314 in the distal direction with respect to the jaws 310, 312 causes the third sections 224 to increase the gap 230 therebetween to accommodate the jaws so that the third sections become seated within the longitudinal trenches 332, 432. The resilient nature of the spring 314, resulting from an increase in the gap 230, exerts a bias force that causes the inclined surfaces 326, 426 of the elongated platforms 320, 420 to be compressed toward one another. Further movement of the spring 314 toward the distal ends 328, 428 of the elongated platforms 320, 420 causes the spacing between the inclined surfaces 326, 426 to decrease and compress the surfaces against the tissue in question, in this case the left atrial appendage.

The further along the spring 314 moves distally with respect to the jaws 310, 312, the greater the moment that is exerted against the inclined surfaces 326, 426 of the elongated platforms 320, 420 because the moment necessary to move the surfaces apart increases as one moves closer to the first section 220. Eventually, movement of the spring 314 toward the distal end 328, 428 of the jaws 310, 312 reaches a point where continued distal movement of the spring is no longer possible.

When the spring 314 reaches the point where further distal movement is no longer possible, the spring is locked into a longitudinal friction fit with respect to the jaws 310, 312. Likewise, when the spring 314 reaches its distal most position, a moment exerted upon the jaws 310, 312 is approximately equal along the moment exerted upon a proximal portion of the jaws via the primary spring 378. Accordingly, compression of the jaws 310, 312 is operative to occlude the tissue clamped between the generally parallel, inclined surfaces 326, 426 of the elongated platforms 320, 420.

In exemplary form, the jaws 310, 312 may be fabricated from any biologically compatible material including, without limitation, ceramics, polymers, metals, alloys of the foregoing, and composites. Likewise, the springs 314, 378 may be fabricated from any resilient material including, without limitation, polymers, metals, and alloy of the foregoing.

In a preferred embodiment, the longitudinal trenches 332, 432 may include a series of depressions that are longitudinally spaced apart from one another and adapted to receive the convex exterior surface 228 of the third spring section 224. In exemplary form, the locations of the depressions may be chosen to balance the moments between the spring 314 and the primary spring 378.

Disassembly of the exemplary occlusion clip 300 includes repositioning the spring 314 proximally with respect to the jaws 310, 312. Eventually, continued proximal movement of the spring 314 with respect to the jaws 310, 312 results in the third sections 224 passing beyond the proximal most portion of the jaws, resulting in complete disengagement between the jaws and spring.

Figure 18:
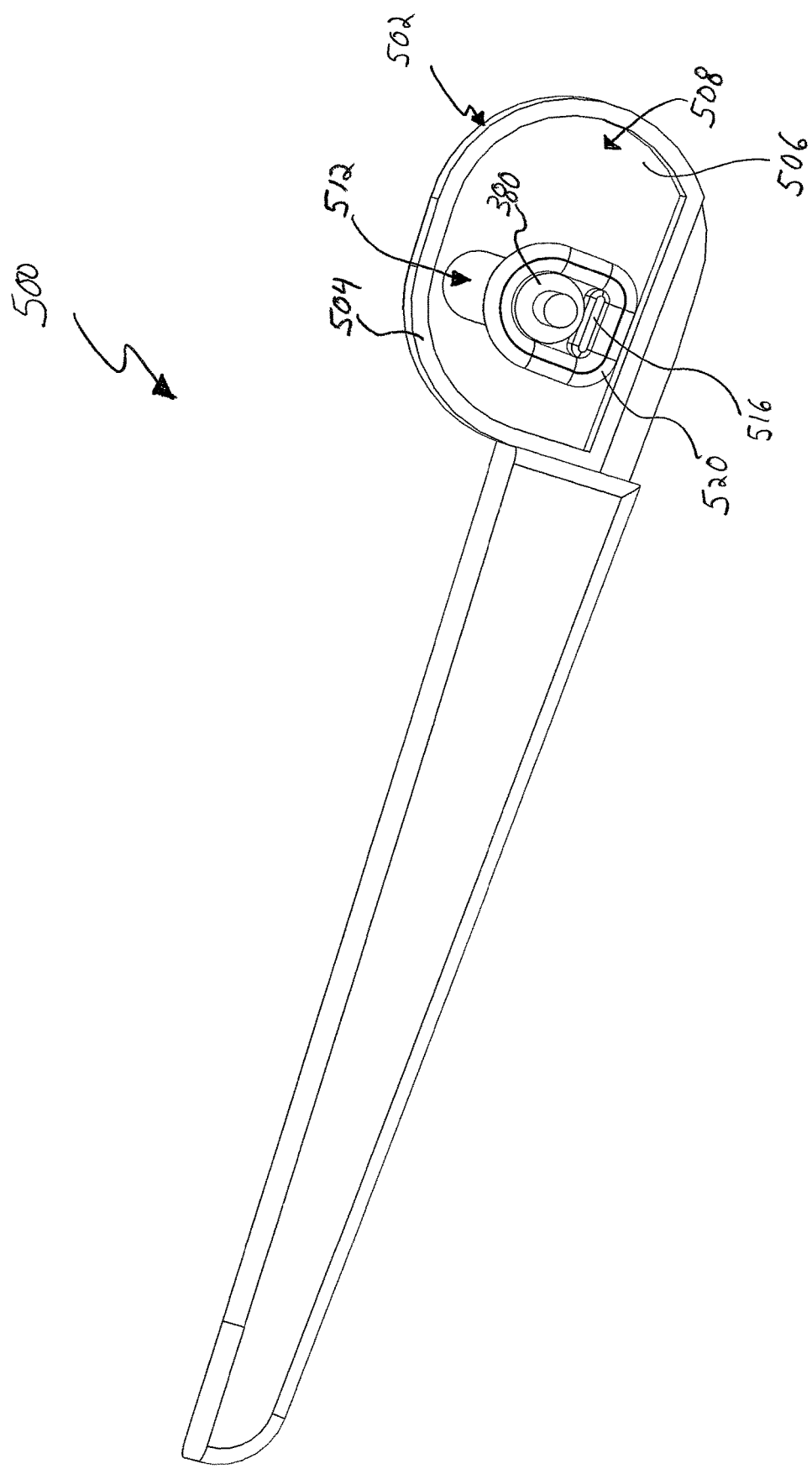
FIG. 18 is an elevated perspective view from the left of an alternate first jaw that may be used in lieu of the first jaw with the occlusion clip of FIG. 9, shown with an alternate first secondary spring and pin mounted to the alternate first jaw.
Figure 19:
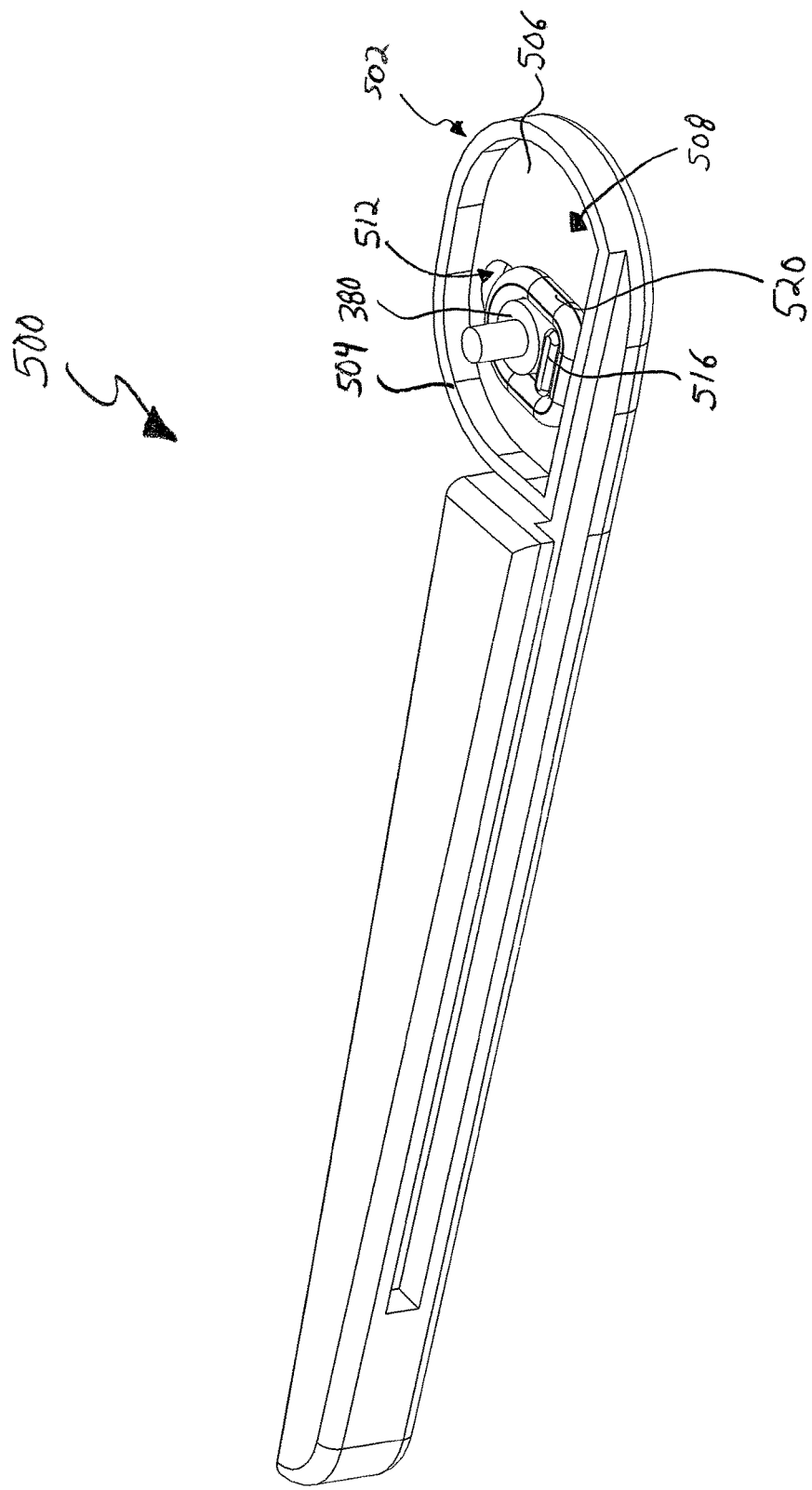
FIG. 19 is a bottom perspective view from the left of the alternate first jaw of FIG. 18.

Referring to FIGS. 18 and 19, an alternate exemplary first jaw 500 that may be used in place of the first jaw 310 as part of the second exemplary occlusion clip 300. In this alternate exemplary first jaw 500, the hub 502 is different from the hub 322 of the first jaw 310. In particular, the revised hub 502 includes a peripheral flange 504 that cooperates with a lateral interior wall 506 to define an interior cavity 508. Extending through the lateral interior wall 506 is an oblong through opening 512 configured to receive a cylindrical pin 380. In this manner, the shape of the through opening 512 allows vertical travel of the cylindrical pin 380 with respect to the first jaw 500.

Proximate the bottom of the oblong opening 512 and extending from the interior wall 506 is a platform 516. This platform 516 and the cylindrical pin 380 are concurrently circumscribed by an elastic band 520 that operates to exert a bias on the proximal aspects of the jaws 500, 312 when coupled to one another. By way of example, the resilient band 520 may be fabricated from any elastic material. In particular, the elastic band 520 resists vertical movement of the cylindrical pin 380 away from the platform. Vertical motion between the cylindrical pin 380 and the platform 516 causes the vertical spacing to change between the jaws 500, 312 at the proximal ends of the jaws. More specifically, a relatively larger vertical spacing between the cylindrical pin 380 and the platform 516 corresponds to a larger vertical spacing between proximal portions of the jaws 500, 312, whereas a relatively smaller vertical spacing between the cylindrical pin and the platform corresponds to a smaller vertical spacing between proximal portions of the jaws. Accordingly, this jaw 500 provides an alternate configuration for using an elastic band 520, as opposed to using the primary spring 378 and the first jaw 310, in combination with the second jaw 312 to form an alternate exemplary occlusion clip.

It is also within the scope of the invention for the exemplary occlusion clips to be shrouded in a tissue ingrowth material. For example, the exemplary occlusion clips may be encased in a C-shaped, loop sleeve that is cylindrical and closed at opposing ends in order to accommodate opening and closing of the exemplary clips (i.e., separation or spacing between the open ends sufficient to position tissue between portions of the clips). Those skilled in the art are familiar with tissue ingrowth materials such as porous fabrics, including Gore Dualmesh (available from W.L. Gore & Associates, www.gore.com) that may be used as to shroud the foregoing exemplary embodiments.

Following from the foregoing description, it should be apparent to those of ordinary skill in the art that, while the methods and apparatuses herein described constitute exemplary embodiments of the present invention, it is to be understood that the inventions described herein are not limited to the above precise embodiments and that changes may be made without departing from the scope of the invention as defined by the following claims. Likewise, it is to be understood that it is not necessary to meet any or all of the identified advantages or objects of the invention disclosed herein in order to fall within the scope of the claims, since inherent and/or unforeseen advantages of the present invention may exist even though they may not have been explicitly discussed herein.

What is claimed is:

1. An occlusion clamp comprising:
a first jaw including a first occlusion surface and a first projection;
a second jaw repositionably mounted to the first jaw, the second jaw including a second occlusion surface and a first track;
a primary spring removably coupled to the first jaw and the second jaw to exert a first bias acting on proximal ends of the first and second jaws; and,
a secondary spring removably coupled to the first jaw and the second jaw to exert a second bias acting on distal ends of the first and second jaws;
wherein the first projection is operatively coupled to the primary spring and is received by the first track so as to allow pivotal and radial repositioning of the first jaw with respect to the second jaw.

2. The occlusion clamp of claim 1, wherein:
the first jaw includes a first elongated platform having a dominant lengthwise dimension; and
the second jaw includes a second elongated platform having a dominant lengthwise dimension and vertically overlaps the first elongated platform.

3. The occlusion clamp of claim 2, wherein:
the first jaw includes a first hub extending from the first elongated platform in the lengthwise dimension, the first hub having a widthwise dimension perpendicular to the lengthwise dimension that is less than a widthwise dimension of the first elongated platform;

the first hub includes a height dimension perpendicular to the lengthwise dimension and the widthwise dimension, the height dimension of the first hub being greater than a height dimension of the first elongated platform;

the second jaw includes a second hub extending from the second elongated platform in the lengthwise dimension, the second hub having a widthwise dimension perpendicular to the lengthwise dimension that is less than a widthwise dimension of the second elongated platform; and, the second hub includes a height dimension perpendicular to the lengthwise dimension and the widthwise dimension, the height dimension of the second hub being greater than a height dimension of the second elongated platform.

4. The occlusion clamp of claim 2, wherein:
the first jaw includes a first hub extending from the first elongated platform;
the second jaw includes a second hub extending from the second elongated platform; and,
the first hub horizontally overlaps the second hub.

5. The occlusion clamp of claim 1, wherein the primary spring includes a U-shaped portion.

6. The occlusion clamp of claim 1, wherein the primary spring comprises a discontinuous loop.

7. The occlusion clamp of claim 1, wherein the primary spring is fabricated from at least one of a polymer, a composite, and a metal.

8. The occlusion clamp of claim 1, wherein:
the primary spring is configured to exert a first bias to retard radial repositioning between the first jaw and the second jaw; and,
the secondary spring is configured to exert a second bias to retard pivotal repositioning between the first jaw and the second jaw.

9. The occlusion clamp of claim 1, wherein the secondary spring includes a U-shaped portion.

10. The occlusion clamp of claim 1, wherein the secondary spring comprises a discontinuous loop.

11. The occlusion clamp of claim 1,
wherein:
the first jaw includes a first hub;
the second jaw includes a second hub; and,
the first hub to horizontally overlaps the second hub so the primary spring interposes the first and second jaws.

12. The occlusion clamp of claim 1, wherein:
the first occlusion surface is substantially planar;
the second occlusion surface is substantially planar;
a lengthwise dimension of the first occlusion surface is larger than a widthwise dimension perpendicular to the lengthwise dimension;
a lengthwise dimension of the second occlusion surface is larger than a widthwise dimension of the second occlusion surface perpendicular to the lengthwise dimension.

13. The occlusion clamp of claim 1, wherein the secondary spring is fabricated from at least one of a polymer, a composite, and a metal.

14. An occlusion clamp comprising:
a first jaw including a first occlusion surface;
a second jaw repositionably mounted to the first jaw, the second jaw including a second occlusion surface;
a primary spring removably coupled to the first jaw and the second jaw to exert a first bias acting on proximal ends of the first and second jaws;
a secondary spring removably coupled to the first jaw and the second jaw to exert a second bias acting on distal ends of the first and second jaws; and,
a pin mounted to the second jaw, wherein the first jaw includes an orifice sized to allow at least partial throughput of the pin and radial movement of the pin within a boundary of the orifice.

15. The occlusion clamp of claim 14, wherein:
at least a portion of the pin includes a circular cross-section; and,
the second jaw includes a cavity receiving a projection of the pin in a friction fit to mount the pin to the second jaw.

16. The occlusion clamp of claim 14, wherein:
at least a portion of the pin includes a circular cross-section; and,
the second jaw includes a projection received by a cavity of the pin to mount the pin to the second jaw via a friction fit.

17. The occlusion clamp of claim 14, wherein:
the first jaw includes a first elongated platform and a first hub;
the second jaw includes a second elongated platform and a second hub;
the first hub includes a cavity sized to house the primary spring; and,
the primary spring is concurrently mounted to the first hub and at least one of the second hub and the pin.

18. An occlusion clamp comprising:
a first jaw including a first occlusion surface;
a second jaw repositionably mounted to the first jaw, the second jaw including a second occlusion surface;
a primary spring removably coupled to the first jaw and the second jaw to exert a first bias acting on proximal ends of the first and second jaws; and,
a secondary spring removably coupled to the first jaw and the second jaw to exert a second bias acting on distal ends of the first and second jaws; wherein:
the first jaw includes a first trench;
the second jaw includes a second trench; and,
the secondary spring is received concurrently with the first trench and the second trench when coupled to the first jaw and the second jaw.

\* \* \* \* \*